(12) United States Patent
Moore et al.

(10) Patent No.: US 12,201,288 B2
(45) Date of Patent: Jan. 21, 2025

(54) FREE MOTION LAPAROSCOPIC SURGICAL SYSTEM

(71) Applicant: The Penn State Research Foundation, Uinversity Park, PA (US)

(72) Inventors: Jason Moore, University Park, PA (US); Samson Galvin, University Park, PA (US); Paris Von Lockette, University Park, PA (US)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 0 days.

(21) Appl. No.: 18/692,696

(22) PCT Filed: Sep. 12, 2022

(86) PCT No.: PCT/US2022/043188
§ 371 (c)(1),
(2) Date: Mar. 15, 2024

(87) PCT Pub. No.: WO2023/043693
PCT Pub. Date: Mar. 23, 2023

(65) Prior Publication Data
US 2024/0325014 A1    Oct. 3, 2024

Related U.S. Application Data

(60) Provisional application No. 63/246,063, filed on Sep. 20, 2021.

(51) Int. Cl.
*A61B 17/02* (2006.01)
*A61B 17/00* (2006.01)

(52) U.S. Cl.
CPC ............ *A61B 17/0218* (2013.01); *A61B 2017/00283* (2013.01); *A61B 2017/00876* (2013.01); *A61B 2562/0247* (2013.01)

(58) Field of Classification Search
CPC ........ B25J 9/1045; B25J 13/02; B25J 13/085; B25J 15/0019; B25J 17/0283; B25J 18/04;
(Continued)

(56) References Cited

U.S. PATENT DOCUMENTS

| 2003/0018270 A1 | 1/2003 | Makin et al. |
| 2009/0005636 A1 | 1/2009 | Pang et al. |

(Continued)

FOREIGN PATENT DOCUMENTS

WO    2008131128 A1    10/2008

OTHER PUBLICATIONS

International Search Report and Written Opinion for PCT/US2022/043188 filed Sep. 12, 2022, date Dec. 22, 2022.

*Primary Examiner* — Scott Luan
(74) *Attorney, Agent, or Firm* — Buchanan Ingersoll & Rooney PC

(57) ABSTRACT

Embodiments relate to a laparoscopic apparatus having a first component and a second component. The first component has a first component manipulation end configured for manipulation by a user and/or a machine, a first component interface end, a first component magnet located at or near the first component interface end, and a first component actuator system including a cable. The first component actuator system is configured to transfer control movements from the first component manipulation end into moments and forces acting upon the cable. The second component has a second component working end configured for performing surgical work, a second component interface end, a second component magnet located at or near the second component interface end, and a second component actuator system (Continued)

configured to transfer moments and forces acting upon the cable into mechanical movements acting upon the second component working end.

20 Claims, 17 Drawing Sheets

(58) Field of Classification Search
CPC .......... B25J 9/10; G05B 15/02; F16H 19/005; F16H 19/0672; F16H 2019/0668; F16H 2019/0677; F16H 55/52; A61B 2017/00876; A61B 10/0233; A61B 17/00234; A61B 2034/302; A61B 34/30; A61B 1/313; A61B 17/22012; A61B 17/2202; A61B 17/29; A61B 17/3417; A61B 17/3423; A61B 2017/00283; A61B 2017/00411; A61B 2017/00464; A61B 2017/00477; A61B 2017/320093; A61B 2017/3484; A61B 2034/731; A61B 2090/371; A61B 2090/378; A61B 2090/3784; A61B 2090/3929; A61B 2090/3975; A61B 34/71; A61B 34/73; A61B 34/76; A61B 8/12; A61B 8/445; A61B 8/4488; A61B 90/10; A61B 90/30
See application file for complete search history.

(56) References Cited

U.S. PATENT DOCUMENTS

| | | |
|---|---|---|
| 2014/0358162 A1 | 12/2014 | Valdastri et al. |
| 2016/0045273 A1 | 2/2016 | Campbell et al. |

FREE MOTION LAPAROSCOPIC SURGICAL SYSTEM

CROSS-REFERENCE TO RELATED APPLICATIONS

This patent application is a U.S. national stage application under 35 U.S.C. § 371 for International Patent Application No. PCT/US2022/043188, filed Sep. 12, 2022, which is related to and claims the benefit of priority to U.S. provisional application 63/246,063, filed on Sep. 20, 2021, the contents of which is each incorporated herein by reference in its entirety.

FIELD OF THE INVENTION

Embodiments relate to a free motion laparoscopic surgical system and methods of use thereof.

BACKGROUND OF THE INVENTION

Traditional laparoscopic surgery involves multiple incisions in the abdomen and highly limited tool mobility. Limited tool mobility causes procedures to take longer time than necessary, requires an extremely high level of surgical skill, and sometimes necessitates additional incisions be made or enlarged. Multiple incisions cause poor cosmetic outcomes, increase patient recovery time, increase patient pain, increase risk of vessel trauma, increase risk of infection, and increase risk of hernias. Developments of Natural Orifice Translumenal Endoscopic Surgery (NOTES) and single-port laparoscopic surgery have been made to reduce incision trauma to the patient. However, these procedures suffer from even greater limited mobility challenges.

BRIEF SUMMARY OF THE INVENTION

A free motion laparoscopic surgical system can be configured to provide single incision, free motion (SIFM) laparoscopic surgery (e.g. use of only a single incision). Unlike traditional laparoscopic surgery, embodiments of SIFM can offer freedom of motion, single incision, and user-friendly controls. No other system in research or on the market allows for high mobility tissue manipulation with a single small minimally invasive incision. Embodiments of the SIFM design can offer numerous healthcare benefits including shorter procedure time, better cosmetic outcomes, decrease patient recovery time, reduce patient pain, reduce risk of vessel trauma, reduce risk of infection, and reduce risk of hernias. The freedom of motion and user-friendly controls can greatly reduce the required skill for the surgeon, thereby allowing for expanded adoption of this beneficial surgical system.

Embodiments of the SIFM can be designed and configured to specifically target gathering preliminary data. Detailed experiments can also be designed to optimize and validate the technology, development of a broad force model, collection of diverse computer tomography (CT) patient anatomy measurements, and demonstrate a functional SIFM device. Embodiments can utilize an effective magnetic holding system that allows for both holding stability and low friction sliding over skin surface, and an effective low profile-controlled motion system for controlling motion of the SIFM device.

Embodiments can be configured to utilize data obtained from at least one human study to effectively test and optimize the system's user performance and user interaction with surgeons. Embodiments of the SIFM system can allow for free movement of the tools over the body surface, like that of open surgery. Embodiments can be configured to require only a single incision for access the human body for a procedure, thereby minimizing patient trauma. This can be achieved, for example, using magnetics to hold tools under the skin and allow translational movement across the skin surface. Hydraulic, electric motor, and cable actuation can allow the under-skin tools to operate the end effector, tilt, extend, and retract to accurately manipulate tissue. The precise movement of the tools can be controlled by the user above the skin or with a robotic system using intuitive user-friendly controls.

Embodiments can be configured to account for plate friction on porcine skin to optimize plate texture, shape, and lubrication for minimized friction design. The magnetic system that uses permanent and electromagnets can be fabricated, and performance assessed as well to optimize both stability and frictional force during sliding.

Embodiments of the control system can utilize a geometric model formed to estimate the working space during insufflation. This information can be used to determine the tool range of motion necessary for performing various laparoscopic surgery procedures. The control system can be based on porcine tissue flexibility data that can allow the system to address how skin may flex during SIFM operation.

The compact low profile motion system of hydraulics, cables, servo motors, etc. can be custom designed and fabricated to maximize both strength and range of motion in some embodiments based on such data or a model developed from such data (e.g. data that relates to the controlled motion system's maximum forces, speeds, and latency of controlled motion to be applied in various different operational modes).

Embodiments of the control system can also be optimized to account for user feedback or user use. For example, medical experts who interact with embodiments of the SIFM and traditional laparoscopic tools in a simulated laparoscopic environment (working vision blocked, laparoscopic camera used, etc.) can provide feedback (e.g. measurements of tool motion can be collected along with interview results) to assess user interaction and facilitate optimization of the control system to improve usability and performance.

In an exemplary embodiment, the laparoscopic apparatus includes a tool comprising a first component and a second component. The first component comprises: a first component manipulation end configured for manipulation by a user and/or a machine; and a first component interface end. The first component includes: a first component magnet located at or near the first component interface end; a first component actuator system including a cable, the first component actuator system configured to transfer control movements from the first component manipulation end into moments and forces acting upon the cable. The second component comprises: a second component working end configured for performing surgical work; and a second component interface end. The second component includes: a second component magnet located at or near the second component interface end; a second component actuator system configured to transfer moments and forces acting upon the cable into mechanical movements acting upon the second component working end.

In some embodiments, the first component is configured for use within an environment outside a human or animal body. The second component is configured for use within an environment inside a human or animal body.

In some embodiments, the second component is configured to be enveloped or engulfed within a cavity of the human or animal body.

In some embodiments, when the first component interface end is placed on or near an outside skin surface of the human or animal body and the second component interface end is placed on or near an inside skin surface of the human or animal body such that the first component magnet and the second component magnet are in proximity to each other so as to allow the first component magnet to impose an attractive force on the second component magnet, the second component becomes coupled with the first component.

In some embodiments, when the second component becomes coupled with the first component, lateral movement, longitudinal movement, rotational movement, and/or tilt movement of the first component is translated to corresponding lateral movement, longitudinal movement, rotational movement, and/or tilt movement for the second component.

In some embodiments, the first component manipulation end includes a handle-actuator configured for use by a human hand and/or an adaptor configured to connect to a mechanical actuator of the machine.

In some embodiments, the second component working end includes an end effector.

In some embodiments, the first component magnet comprises one or more magnets, the second component magnet comprises one or more magnets, and the first component actuator system comprises one or more cables, one or more hydraulic actuators, and/or one or more electric motor actuators.

In some embodiments, the first component interface end and/or the second component interface end includes one or more sensors.

In some embodiments, the one or more sensors include a pressure sensor, a proximity sensor, a movement sensor, magnetometer, magnetic tracker, gyroscope, and/or an accelerometer.

In some embodiments, the apparatus comprises: a first component processor configured to control magnetic force of the first component magnet and/or a second component processor configured to control magnetic force of the second component magnet; and a control module in communication with the first component processor and/or the second component processor, the control module configured to transmit a control signal to the first component processor and/or the second component processor. Magnetic force of the first component magnet is controlled via varying a distance the first component magnet is relative to the second component magnet and/or controlling current supplied to the first component magnet. Magnetic force of the second component magnet is controlled via varying a distance the second component magnet is relative to the first component magnet and/or controlling current supplied to the second component magnet.

In some embodiments, the first component interface end includes a layer comprising polytetrafluoroethylene.

In an exemplary embodiment the laparoscopic apparatus comprises a laparoscope, the laparoscope comprising an actuator system including an actuator and a cable, the actuator system configured to transfer control movements from the actuator into moments and forces acting upon the cable. The apparatus includes a tool comprising a first component and a second component. The first component comprises a first component interface end and a first component magnet located at or near the first component interface end. The second component comprises: a second component working end configured for performing surgical work; and a second component interface end. The second component includes: a second component magnet located at or near the second component interface end; a second component actuator system configured to transfer moments and forces acting upon the cable into mechanical movements acting upon the second component working end.

In some embodiments, the first component is configured for use within an environment outside a human or animal body; and the second component is configured for use within an environment inside a human or animal body.

In some embodiments, the second component is configured to be enveloped or engulfed within a cavity of the human or animal body.

In some embodiments, when the first component interface end is placed on or near an outside skin surface of the human or animal body and the second component interface end is placed on or near an inside skin surface of the human or animal body such that the first component magnet and the second component magnet are in proximity to each other so as to allow the first component magnet to impose an attractive force on the second component magnet, the second component becomes coupled with the first component.

In an exemplary embodiment, a method of preparing for or performing a surgical procedure using a tool comprising a first component and a second component involves inserting the second component into a cavity of a body via an incision, wherein a cable extends from a second component actuator system through the incision and to a first component actuator system. The method involves placing a first component interface end of the first component adjacent an outside skin surface of the body. The method involves allowing a magnet of the first component interface and a magnet of the second component interface to couple the first component with the second component.

In some embodiments the method involves performing surgical work within the body cavity by controlling a working end of the second component via actuation of a manipulation end of the first component.

In some embodiments, actuation of the manipulation end of the first component involves manual actuation via a human and/or automated actuation via a machine.

In some embodiments, controlling lateral movement, longitudinal movement, rotational movement, and/or tilt movement of the second component via a corresponding lateral movement, longitudinal movement, rotational movement, and/or tilt movement of the first component.

Further features, aspects, objects, advantages, and possible applications of the present invention will become apparent from a study of the exemplary embodiments and examples described below, in combination with the Figures, and the appended claims.

BRIEF DESCRIPTION OF THE FIGURES

The above and other objects, aspects, features, advantages, and possible applications of the present invention will be more apparent from the following more particular description thereof, presented in conjunction with the following drawings. It should be understood that like reference numbers used in the drawings may identify like components.

DETAILED DESCRIPTION OF THE INVENTION

The following description is of an embodiment presently contemplated for carrying out the present invention. This description is not to be taken in a limiting sense but is made merely for the purpose of describing the general principles and features of the present invention. The scope of the present invention should be determined with reference to the claims.

Figure 4:
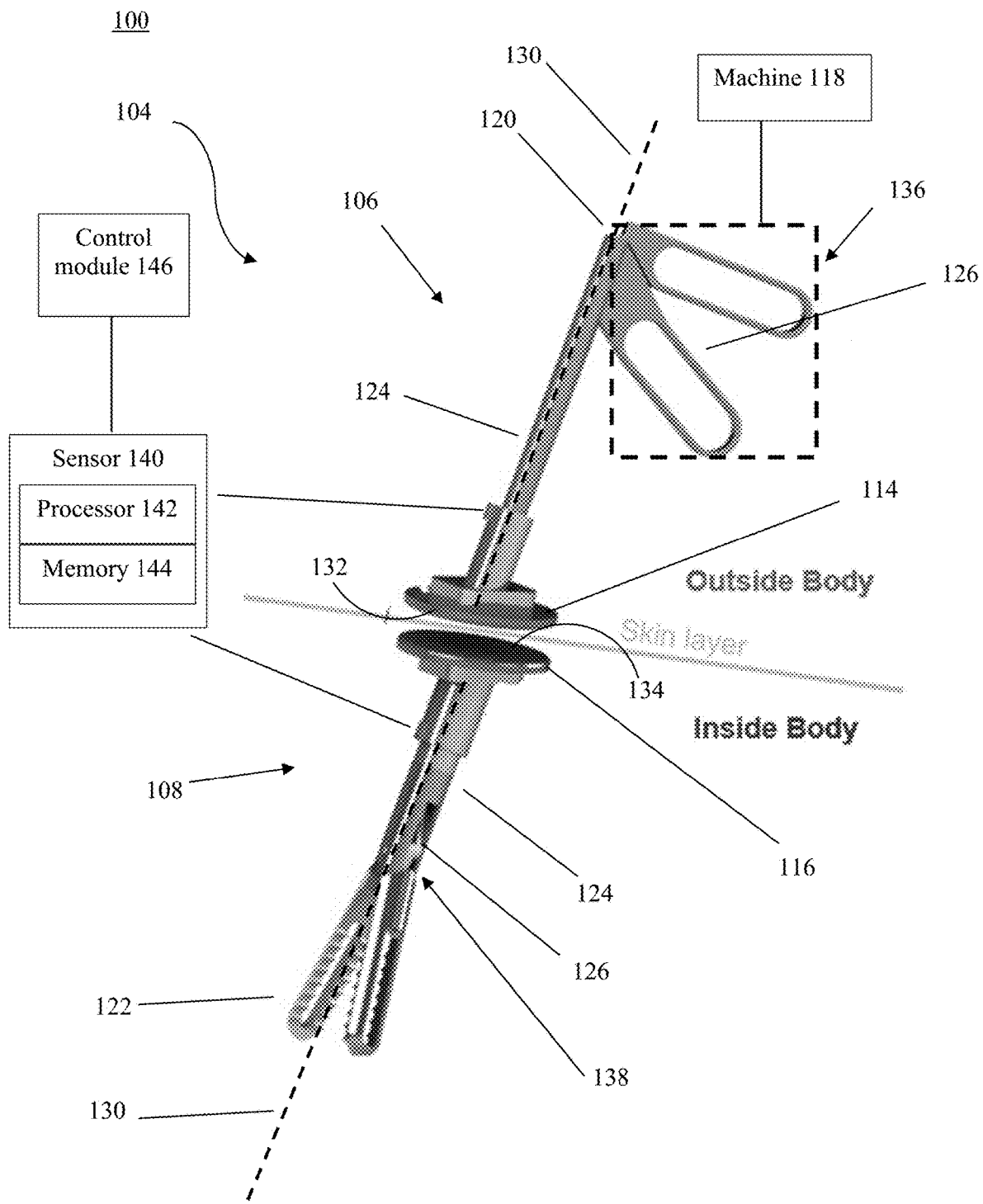
FIG. 4 shows an embodiment of the laparoscopic apparatus.
Figure 7:
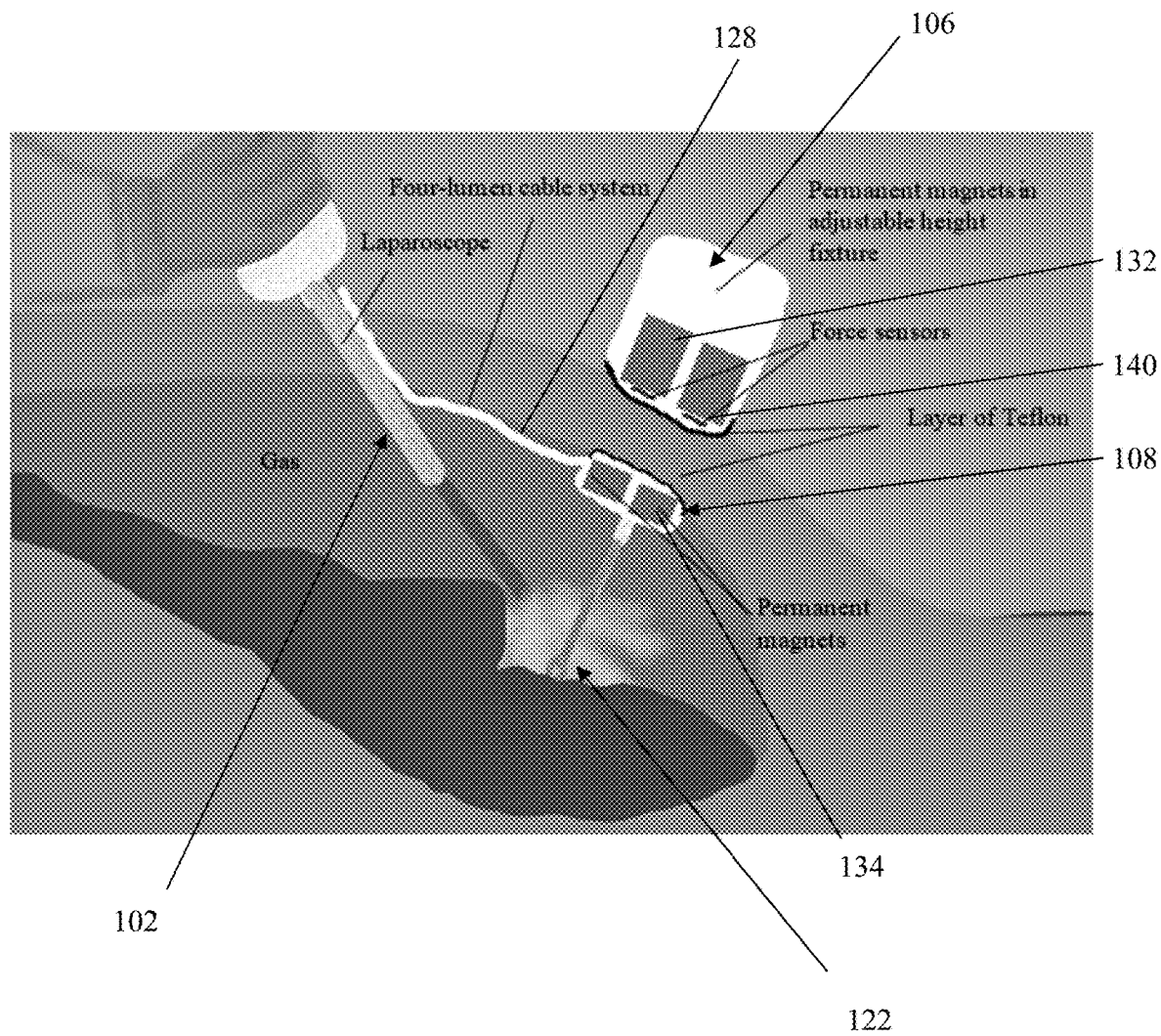
FIG. 7 shows another embodiment of the laparoscopic apparatus.
Figure 8:
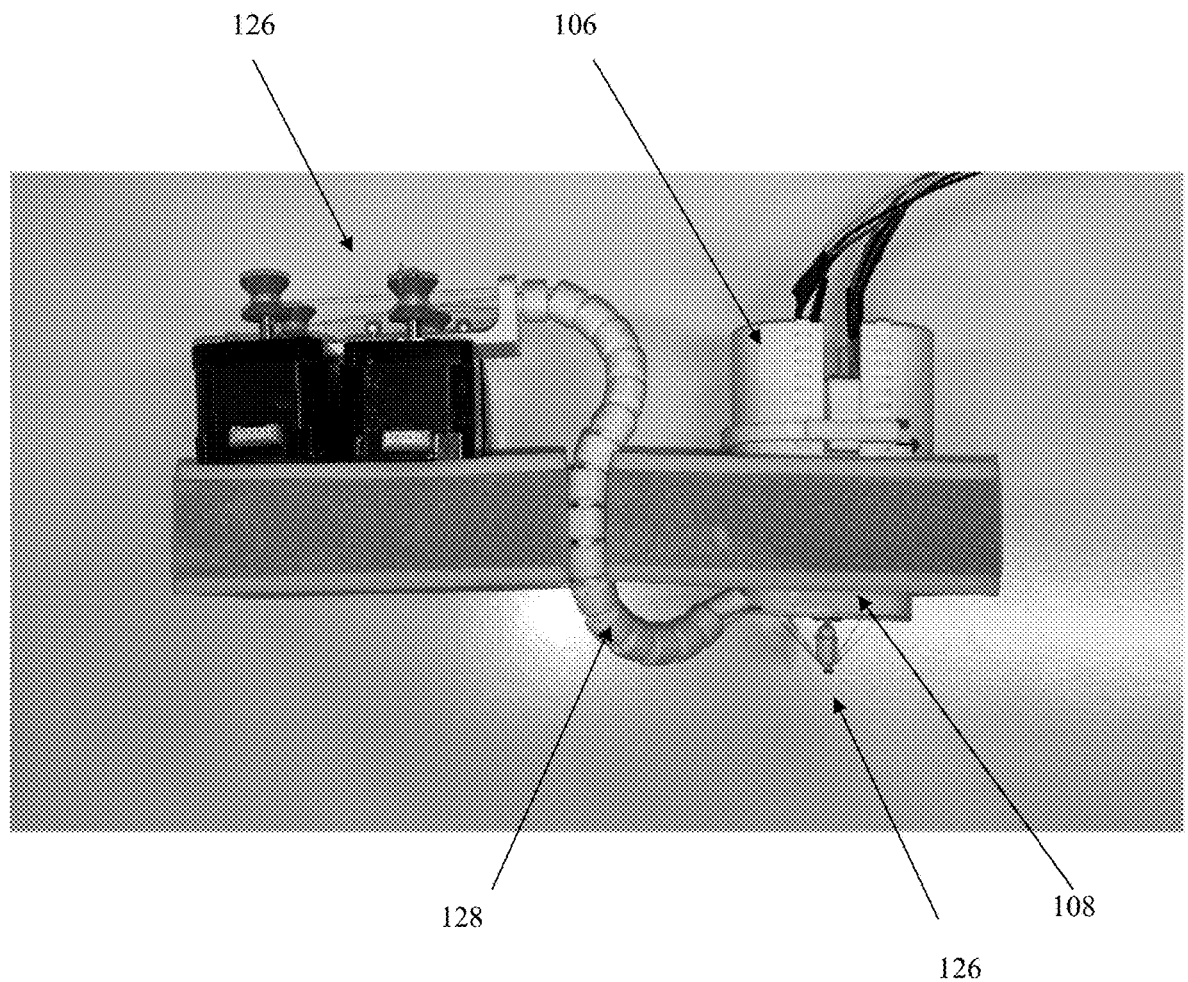
FIG. 8 shows an exemplary design for an embodiment of the apparatus.

Referring to FIGS. 4, 7, and 8, embodiments relate to a laparoscopic apparatus 100. This apparatus 100 may be referred to herein as the single incision, free motion (SIFM) system/apparatus. The laparoscopic apparatus 100 can be configured for performing laparoscopic surgery, a laparoscopic procedure, a laparoscopic operation, or a task associated with laparoscopic surgery, a laparoscopic procedure, or a laparoscopic operation. Generally, laparoscopic surgery involves use of a laparoscope 102 that is inserted into a body cavity 110 of a patient via an incision. The laparoscope 102 is a device having optics, cameras, lighting, sensors, etc. that provide a surgeon a view of the body cavity 110. A tool(s) is/are inserted into other incision(s) to perform surgical tasks within the body cavity 110. A surgeon uses the laparoscope 102 to view the area being worked upon and the tool(s) are used to perform surgical tasks. Laparoscopic surgery typically involves insufflation, which is a procedure to inflate the body cavity 110 with a gas so as to provide a more conducive area of operation or workspace for a surgeon controlling the laparoscope 102 and/or tool(s).

Embodiments of the laparoscopic apparatus 100 can include the laparoscope 102 as part of the apparatus 100 or be used in conjunction with laparoscope 102. As will be explained in more detail herein, the inventive apparatus 100 includes a tool 104 having a first component 106 and a second component 108. The second component 108 includes means for performing surgical tasks within the body cavity 110. It is contemplated for the second component 108 to be inserted completely within the body cavity 110 while the first component 106 remains completely outside the body 112 of the patient. The first component 106 has a first component interface 114 that interfaces with a second component interface 116 so as to couple the first component 106 with the second component 108 but with skin of the patient being located between the first component 106 and the second component 108. The first component 106 can be a device that is merely used to couple with the second component 108 so as to hold the second component in a proper position within the body cavity 110 or facilitate repositioning of the second component 108 within the body cavity 110. (See, e.g., FIG. 7). In that embodiment, the laparoscope 102 can include actuator components (e.g., controls, cables, etc.) that allow a user to control aspects of the second component 108 (e.g., control gripping, cutting, ablation, etc.). Alternatively, the first component 106 can be a device that both: 1) couples with the second component 108 so as to hold the second component in a proper position within the body cavity 110 or facilitate repositioning of the second component 108 within the body cavity 110; and 2) includes actuator components (e.g., controls, cables, etc.) that allow a user to control aspects of the second component 108 (e.g., control gripping, cutting, ablation, etc.). (See, e.g., FIG. 4). In that embodiment, the laparoscope 102 can be used for viewing the body cavity 110 but has no means of control over the second component 108.

It should be understood that while FIG. 4 shows actuator components in or on the first component 106 for controlling the second component 108, the actuator components need not be in or on the first component 106 in that embodiment. For instance, the actuator components can be part of the first component 106, part of the laparoscope 102, or be part of a separate controller (e.g., joystick, computer device, etc.). Similarly, while FIG. 7 shows actuator components in or on the laparoscope 102 for controlling the second component 108, the actuator components need not be in or on the laparoscope 102 in that embodiment. For instance, the actuator components can be part of the first component 106, part of the laparoscope 102, or be part of a separate controller (e.g., joystick, computer device, etc.). The cable(s) 128 in any embodiment can be routed through the incision for the laparoscope 102, the incision for the second component 108, or another incision.

The laparoscopic apparatus 100 comprises a tool 104. The tool 104 can include at least one component. For instance, the tool 104 can include a first component 106, a second component 108, etc. It is contemplated for the tool 104 to include a first component 106 and a second component 108. It is understood that the tool 104 can include one or more first components 106 and one or more second components 108.

In an exemplary embodiment shown in FIG. 4, the first component 106 can be a device configured for manipulation (e.g., grasping, actuation, movement, etc.) by a user and/or a machine 118. For instance, the first component 106 can have a first component manipulation end 120 configured for manipulation by a user and/or a machine 118 (e.g., a robotic device) and a first component interface 114 configured for coupling with the second component 108. For example, the first component 106 can be a handle configured to couple to an end effector (e.g., the second component 108 can be an end effector or include an end effector as its working end 122). The handle may have an actuator 126 configured to actuate gripper portions of the end effector. With such an example, the first component 106 can be a member having a first component manipulation end 120 located at one end of a shaft 124 and a first component interface 114 located at the opposite end of the shaft 124. The first component manipulation end 120 can be a handle with an actuator 126. The actuator 126 can be in mechanical connection with at least one cable 128 routed through, over, or along the shaft 124. The cable 128 can extend from the first component interface 114.

The second component 108 can be a member having a second component working end 122 located at one end of a shaft 124 and a second component interface 116 located at the opposite end of the shaft 124. The cable 128 extending from the first component interface 114 can be routed through the second component interface 116, further routed through, over, or along the shaft 124, and in mechanical connection with the second component working end 122. The second component working end 122 can be an end effector having a set of grippers, for example. Actuation of the actuator 126 of the handle can cause actuation of the grippers.

As another example, the first component manipulation end 120 can include an adapter (e.g., a chuck, a coupling, an interface, a manifold, a console, etc.) configured to mechanically, electrically, or electro-mechanically attach to a motor or actuator of a machine 118. Actuation of the motor or actuator can similarly cause actuation of the grippers.

It is understood that the first component 106 can include any number or arrangement of manually controlled/actuated actuators 126 and/or automatic (e.g., machine 118) controlled/actuated actuators 126 for the first component manipulation end 120. Thus, a first component manipulation end 120 can have both a manually operated handle and an adapter configured to connect to a machine.

As noted herein, the first component 106 can include a first component interface 114 and the second component 108 can include a second component interface 116. It is contemplated for the interface ends 114, 116 to be planar members or substantially planar members so as to allow for forming a flush or substantially flush abutment when the first component interface 114 is made to contact the second component interface 116, or made to couple to each other with skin lying therebetween. While it is contemplated for the interface ends 114, 116 to be flat, other shapes can be used. Whichever shape is selected, it may be beneficial for the shape of the first component interface 114 to complement that of the second component interface 116 so as to facilitate the flush or substantially flush abutment discussed above. In use, the first component interface 114 may not actually abut the second component interface 116, as it is contemplated for the patient's skin to be located between the two interfaces 114, 116, but the complementary shapes can allow for better coupling between the two components 106, 108. Thus, the first component 106 can include a shaft 124 leading to the first component interface 114 that is a planar member attached to or formed on the distal end of the shaft 124. The planar member can be orientated at an angle normal to the longitudinal axis 130 of the shaft 124. Similarly, the second component 108 can include a shaft 124 leading to the second component interface 116 that is a planar member attached to or formed on the distal end of the shaft 124. The planar member can be orientated at an angle normal to the longitudinal axis 130 of the shaft 124.

The first component 106 can include a first component magnet 132 located at or near the first component interface 114. The first component magnet 132 can be part of the first component interface 114 (e.g., the first component interface 114 or at least a portion thereof can be a magnet), formed on the first component interface 114, molded within the first component interface 114, etc. The magnet can be a permanent magnet, temporary magnet, electromagnet, etc. The first component magnet 132 can include one or more magnets.

The first component 106 can include a first component actuator system 136. This can include an actuator 126 and the at least one cable 128. The first component actuator system 136 can be configured to transfer control movements from the first component manipulation end 120 into moments and forces acting upon the cable 128. For instance, actuation of the actuator 126 can cause the cable 128 to retract or extend, or at least create tension forces on the cable 128. Manipulation of the handle can actuate a lever actuator 126, thereby increasing or decreasing tension on the cable 128, which can also retract/extend the cable 128. In the alternative, actuation of the handle can actuate a step motor, servo, etc. that causes the cable 128 to wind/unwind or partially wind/unwind about a spool, thereby retracing/extending the cable 128. It is understood that the machine 118 can act upon similar actuators 124 for automated control of the first component actuator system 136.

The second component 108 can include a second component working end 122 configured for performing surgical work or a surgical task. The second component working end 122 can be a gripper, a laser, a scalpel, etc. The second component can include the second component interface 116 discussed herein.

The second component 108 can include a second component magnet 134 located at or near the second component interface 116. The second component magnet 134 can be part of the second component interface 116 (e.g., the second component interface 116 or at least a portion thereof can be a magnet), formed on the second component interface 116, molded within the second component interface 116, etc. The magnet can be a permanent magnet, temporary magnet, electromagnet, etc. The second component magnet 134 can include one or more magnets.

The second component 108 can include a second component actuator system 138 configured to transfer moments and forces acting upon the cable 128 into mechanical movements acting upon the second component working end 122. For instance, the second component actuator system 138 can include a lever, step motor, servo, etc. configured to transfer moments and forces acting upon the cable 128 into mechanical movements acting upon the second component working end 122. As discussed herein, there can be one or more cables 128. The second component actuator system 138 can include one or more levers, step motors, servos, etc. for each cable 128. Movement of the cable(s) 128 can cause actuation of the one or more levers, step motors, servos, etc. The one or more levers, step motors, servos, etc. can be in mechanical connection with the second component working end 122. As a non-limiting example, one or more cables 128 can extend from the one or more levers, step motors, servos, etc. and connect with the second component working end 122. As another example, one or more levers, step motors, servos, etc. can be in direct mechanical engagement with the second component working end 122.

The first component 106 can be configured for use within an environment outside a patient's (human or animal) body 112. The second component 108 can be configured for use within an environment inside the patient's body 112. For instance, an incision can be made in the patient's body 112 that grants ingress and egress to a body cavity 110 (e.g., an abdomen). The second component 108 can be inserted into the body cavity 110 via the incision. This can involve inserting the second component 108 such that the second component working end 122 spearheads the insertion. It is contemplated for the second component 108 to be configured to be enveloped or engulfed within the body cavity 110 of the patient. The cable(s) 128 extending from the second component interface 116 can extend out from the incision (e.g., the cable(s) 128 can extend out of the patient's body via the incision), wherein the cable(s) 128 are connected to the first component actuator system 136. The second component 108 can be positioned within the body cavity 110 such that the second component interface 116 is adjacent in inside skin surface of the body cavity 110. This can include an inside skin surface at the incision, at a location near the incision, or at a location that is away from the incision. The first component 106 can be positioned outside the patient's body 112 such that the first component interface 114 is placed adjacent the patient's outside skin surface.

The first component 106 can be maneuvered such that the first component interface 114 co-registers (aligns with, is in close proximity with, etc.) with the second component interface 116. Co-registering of the first component interface 114 with the second component interface 116 occurs while the first component 106 is outside the patient and the second component 108 is inside the patient, and thus a layer of skin lies between the first component interface 114 and the second component interface 116. The co-registering may occur at the incision site, and thus there may be at least a portion in which no skin layer exists between the first component interface 114 and the second component interface 116.

When the first component interface 114 is placed on or near an outside skin surface of the patient and the second component interface 116 is placed on or near an inside skin surface of the patient such that the interface ends 114, 116 co-register, the first component magnet 132 and the second component magnet 134 become in proximity to each other. This can allow the first component magnet 132 (or second component magnet 134) to impose an attractive force on the second component magnet 134 (or first component magnet 132). This attractive force, can cause the second component 108 to become coupled (e.g., linked, connected, paired, etc.) with the first component 106. When the second component 108 becomes coupled with the first component 106, lateral movement, longitudinal movement, rotational movement, and/or tilt movement of the first component 106 is translated to corresponding lateral movement, longitudinal movement, rotational movement, and/or tilt movement for the second component 108. For instance, the first component 106 can be moved laterally (e.g., parallel relative to the outside skin surface) so as to translate the first component 106 across the outside skin surface, which will cause the second component 108 to move laterally (e.g., parallel relative to the inside skin surface) so as to translate the second component 108 across the inside skin surface. The first component 106 can be moved longitudinally (e.g., perpendicular relative to the outside skin surface) so as to move the first component 106 towards or away from the body cavity 110, which will cause the second component 108 to move longitudinally (e.g., perpendicular relative to the inside skin surface) so as to move the second component 108 in a corresponding manner. The first component 106 can be rotated about its longitudinal axis 130, which will cause the second component 108 to rotate in a corresponding manner. The first component 106 can be titled, which will cause the second component 108 to tilt in a corresponding manner.

The first component actuator system 136 can include one or more cables 128, levers, step motors, servos, etc. The second component actuator system 138 can include one or more cables 128, levers, step motors, servos, etc. This can facilitate more fine-tuned control of the second component working end 122 (e.g., one cable 128 may control rough movement of the grippers, another cable 128 can control finer movement of the same, etc.), independent control of different aspects of the second component working end 122 (one cable 128 may control splay movement of grippers, another cable 128 may control contraction movement of the gripper, another cable 128 may control rotational movement of the grippers, etc.), etc.

The first component interface 114 and/or the second component interface 116 can include one or more sensors 140. The sensor 140 can be disposed in or on a portion of the interface end 114, 116, the shaft, etc. The sensor 140 can be a pressure sensor, a proximity sensor, a movement sensor, magnetometer, magnetic tracker, gyroscope, an accelerometer, etc. The sensor 140 can be configured to measure pressure between the interface end 114, 116 and the skin as a proxy for how well the two components 106, 108 are coupled, measure proximity of one interface end 114, 116 to another interface end 114, 116, measure proximity of an interface end 114, 116 to skin, measure movement of one component 106, 108 relative to the other component 106, 108, measure tilt, rotation etc. of a component 106, 108, etc.

The sensor 140 can include or be in communication (hardwired or wireless) with a processor 142. The processor 142 can receive measurement data from the sensor 140, process the measurement data, store the measurement data, display measurement data, etc. The processor 142 can be part of or in communication with a machine (e.g., a computer device, a logic device, a circuit, an operating module (hardware, software, and/or firmware), etc.). The processor 142 can be hardware (e.g., processor, integrated circuit, central processing unit, microprocessor, core processor, computer device, etc.), firmware, software, etc. configured to perform operations by execution of instructions embodied in algorithms, data processing program logic, artificial intelligence programming, automated reasoning programming, etc. The processor 142 can receive, process, and/or store readings from the sensor 140.

It should be noted that use of processors 142 herein can include any one or combination of a Graphics Processing Unit (GPU), a Field Programmable Gate Array (FPGA), a Central Processing Unit (CPU), etc. The processor 142 can include one or more processing or operating modules. A processing or operating module can be a software or firmware operating module configured to implement any of the functions disclosed herein. The processing or operating module can be embodied as software and stored in memory, the memory being operatively associated with the processor 142. A processing module can be embodied as a web application, a desktop application, a console application, etc.

The processor 142 can include or be associated with a computer or machine readable medium. The computer or machine readable medium can include memory 144. Any of the memory 144 discussed herein can be computer readable memory configured to store data. The memory 144 can include a volatile or non-volatile, transitory or non-transitory memory, and be embodied as an in-memory, an active memory, a cloud memory, etc. Embodiments of the memory 144 can include a processor module and other circuitry to allow for the transfer of data to and from the memory 144, which can include to and from other components of a communication system. This transfer can be via hardwire or wireless transmission. The communication system can include transceivers, which can be used in combination with switches, receivers, transmitters, routers, gateways, waveguides, etc. to facilitate communications via a communication approach or protocol for controlled and coordinated signal transmission and processing to any other component or combination of components of the communication system. The transmission can be via a communication link. The communication link can be electronic-based, optical-based, opto-electronic-based, quantum-based, etc.

The computer or machine readable medium can be configured to store one or more instructions thereon. The instructions can be in the form of algorithms, program logic, etc. that cause the processor 142 to execute any of the functions disclosed herein.

There can be any number of processors 142. For instance, there can be one processor 142 for the tool 104, a processor 142 for the first component 106, a processor 142 for the second component 108, etc.

The processor 142 can be in communication with other processors of other devices (e.g., a computer device, a computer system, a laptop computer, a desktop computer, etc.). An exemplary other device can be a computer with a display screen. Any of the other devices can include any of the exemplary processors disclosed herein. Any of the processors can have transceivers or other communication devices/circuitry to facilitate transmission and reception of wireless signals. Any of the processors can include an Application Programming Interface (API) as a software intermediary that allows two or more applications to talk to each other. Use of an API can allow software of the processor 142 to communicate with software of a processor of the other device(s).

The processor 142 of the sensor 140 can be in communication with the processor of the other device. The other device can include software such as graphics display software, analytical software, etc. that uses sensor readings from the sensor 140 as inputs. For instance, the processor 142 of the sensor can transmit signals to the processor of the other device. This can be a push or pull operation. The sensor 140 can transmit the sensor readings continuously, periodically, as requested by a user of the other device, as-needed via determination of an algorithm embedded in the other device, etc.

As noted herein, the processor 142 can be a device separate from the sensor 140. For instance, the processor 142 may be on the first component 106, may be one the second component 108, may be a device that is separate from the tool 104, etc. In an exemplary embodiment, the processor 142 is disposed on a portion of the first component 106 and is in hardwired communication with the sensor 140 via a cable 128 (e.g., one of the cables 128 can be an electrical line). The processor 142 can then be in communication (hardwired or wireless) with another processor of a device (e.g., a computer with a display screen). In addition, or in the alternative, the processor 142 can be in communication (hardwired or wireless) with another processor of a device that is the machine 118. The sensor 140 can provide feedback to the machine 118 or to allow the machine 118 to intelligently control the tool 104. Similarly, the sensor 140 can provide visual and analytical feedback to a user via a computer display (e.g., the sensor 140 can provide signals to a processor of a device that is a computer display).

As noted herein, any of the magnets can be electromagnets. This can be done to facilitate control of magnetic force applied via the first component magnet 132 and/or second component magnet 134. A variable control circuit or motor can be used to control the amount of magnetic force generated by any of the magnets. This variable control circuit or motor can be in communication (hardwired or wireless) with the processor 142. Control algorithms can be used to allow the processor 142 to control the magnetic forces applied. There can be a processor 142 for each component 106, 108 so as to independently control magnets of each component 106, 108. For instance, there can be a first component processor 142 configured to control magnetic force of the first component magnet 132 and/or a second component processor 142 configured to control magnetic force of the second component magnet 132. In addition or in the alternative, the apparatus 100 can include a control module 146. The control module 146 can be in communication (hardwired or wireless) with any of the processors 142 and configured to transmit a control signal to the processor 142 so as to allow a user to control the magnetic force applied. The control module 146 can be a graphical user interface displayed on a display of a computer device, for example.

In addition or in the alternative to the variable control of electromagnets, the apparatus 100 can use permanent magnets with a variable height control mechanism. The variable height control mechanism can be an actuator in connection with a platform, the platform being connected to the interface 114, 116. The magnets can be attached to, molded in, or be part of the platform. Actuating the actuator can cause the platform to raise or lower, thereby adjusting the distance (or height) that the magnet is relative to the interface 114, 116. Adjusting this distance can be done to adjust the magnetic force the magnet located on one interface 114, 116 imposes on the magnet located on the other interface 114, 116.

As noted herein, it is contemplated for the first component 106 to be placed adjacent the patient's body such that the first component interface 114 is against the patient's outside skin. It is further contemplated to maneuver the first component 106 (e.g., lateral movement, longitudinal movement, rotational movement, and/or tilt movement) so as to provide the benefit of free motion during surgery. With this in mind, it may be beneficial to dispose a friction reducing material on the first component interface 114 and/or the second component interface 116 so as to reduce friction between the interface 114, 116 and the patient's skin, or alternatively place a layer of friction reducing material between the interface 114, 116 and the skin. This friction reducing material can be silicone, polytetrafluoroethylene, a powder, etc.

In the exemplary embodiment shown in FIG. 7, the laparoscopic apparatus 100 includes a laparoscope 102. The laparoscope 102 can have an actuator system including an actuator 126 and a cable 128 similar to the actuator system of the first component 106 discussed in the embodiment of FIG. 4. The actuator system can be configured to transfer control movements from the actuator into moments and forces acting upon the cable 128. The apparatus includes a tool 104 comprising a first component 106 and a second component 108. The first component 106 has a first component interface 114 and a first component magnet 132 located at or near the first component interface 114. The second component 108 has a second component working end 122 configured for performing surgical work and a second component interface 116. The second component 108 also includes a second component magnet 134 located at or near the second component interface 116, a second component actuator system 138 being configured to transfer moments and forces acting upon the cable 128 into mechanical movements acting upon the second component working end 122.

Details of the component parts of this embodiment (shown in FIG. 7) can be the same or similar to those of the embodiment shown in FIG. 4, except that with this embodiment the actuator system controlling the second component working end 122 is located in or on the laparoscope 102 as opposed to the first component 106. In this embodiment, the first component 106 is merely used to create a coupling arrangement with the second component 108 and allow for providing lateral movement, longitudinal movement, rotational movement, and/or tilt movement to the second component 108. The control of the second component working end 122 is achieved via the actuator system of the laparoscope 102. The cable(s) 128 from the actuator 126 can be routed along the probe or tube portion of the laparoscope 102 and extend to the second component 108. Thus, an incision is made, wherein the second component 108 is inserted therethrough and positioned within the body cavity 110. The first component 106 is used to create a coupling arrangement with the second component 108. A second incision is made for the laparoscope 102. Cable(s) 128 from the laparoscope 102 are routed through the second incision and to the second component 108. Control of the second component working end 122 can be achieved via the actuator 126 of the laparoscope 102, whereas movement or non-movement of the second component 108 is controlled via manipulation of the first component 106.

Any of the actuators 126 disclosed herein can be manual, mechanical, electronic, electro-mechanical, hydraulic, pneumatic, etc. It is contemplated for the actuators 126 and actuator systems 136, 138 (especially those of the second component 108) to be of a low profile so as to minimize occupation of space and obstruction for a surgeon performing work on the patient.

EXAMPLES

Exemplary embodiments of the apparatus 100 and test results are presented below.

Example 1

Figure 1:
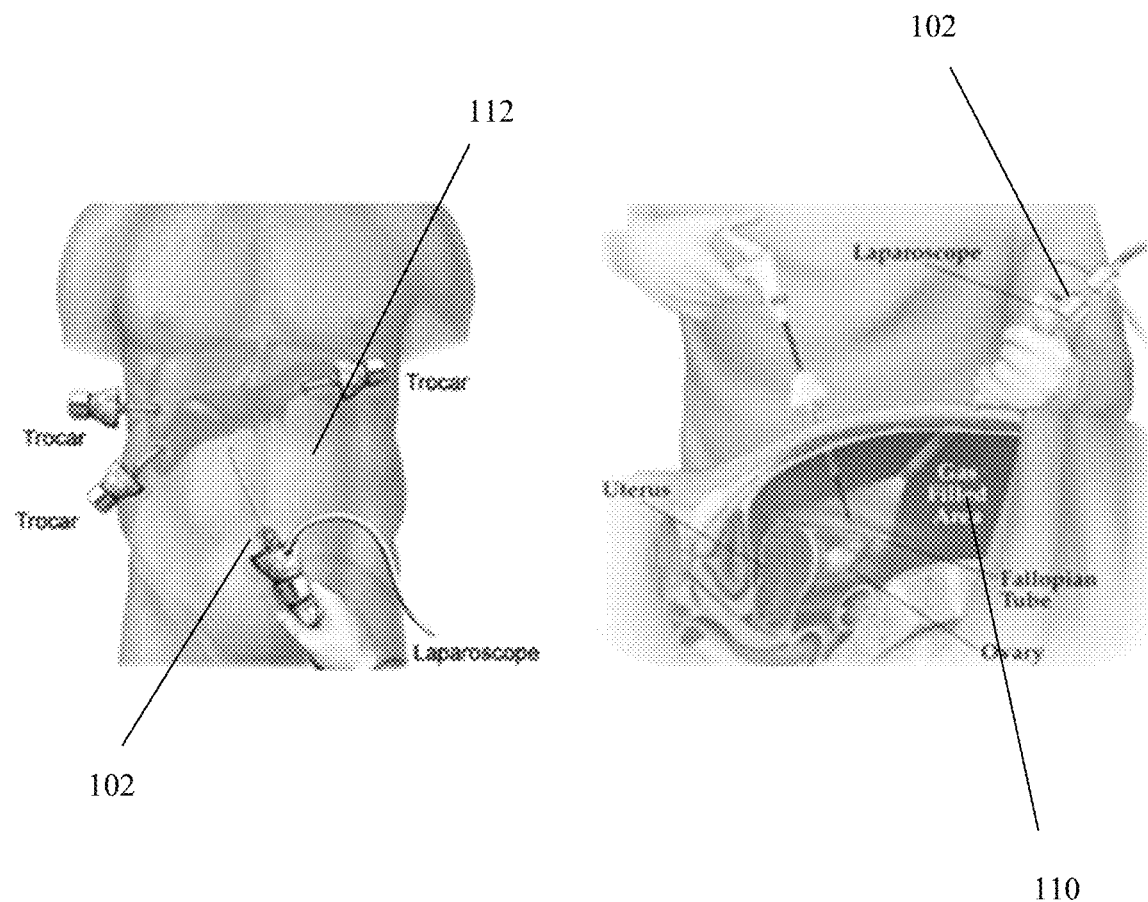
FIG. 1 illustrates a typical laparoscopic surgery.

Every year approximately 15 million laparoscopic procedures are performed globally, including 4.8 million in the United States. Laparoscopic surgical approach generally requires three to five 1~2 cm keyhole incisions, if done successfully, to be made at varying locations while the abdominal space is expanded with pressurized $CO_2$ gas as shown FIG. 1. This approach offers significant advantage over traditional open surgery including reducing surgical site infections, reduced scaring, reduced patient pain, and shortened patient recovery time. Over the last thirty years these benefits have led to the laparoscopic surgical approach being used in numerous procedures including: cholecystectomy, appendectomy, hernia repair, bowel resection, even more complicated procedures such as gastric bypass, and a range of other therapeutic and diagnostic procedures.

Laparoscopic surgery can face significant mobility challenges because the port location is fixed to the body where the incision is made. Therefore, the tools and instruments must all pivot around individual port locations, significantly limiting the mobility and complicating the necessary user controls compared to open surgery. As a result, laparoscopic surgery times are longer compared to open surgery; one study notes average of 30 min more time needed compared to open surgery for performing a laparoscopic colectomy. Laparoscopic surgery can also be more stressful for surgeons and involves significantly longer training time; for laparoscopic prostatectomy one study showed 200 to 250 patient cases are needed to gain full proficiency.

Although laparoscopic approach offers minimal scaring compared to open surgery it still creates a series of scars for each incision port made. As expected, fewer ports results in noticeably better cosmetic outcomes. Although typically only three to five 1~2 cm keyhole incisions are created the lack of mobility sometimes necessitates the doctor to lengthen and add more incisions during the procedure. In addition to poor cosmetic outcomes, more incisions increases patient recovery time, patient pain, risk of vessel trauma, risk of infection, and risk of hernias which occur on average in 0.5% of procedures. Therefore, reducing number of incisions can have a major positive impact on laparoscopic surgery.

It has been determined that state-of-the-art existing tools and approaches for laparoscopic surgery have yet to successfully allow for tool mobility comparable to open surgery, minimally invasive single port access, and user-friendly controls as proposed in this application.

Figure 2:
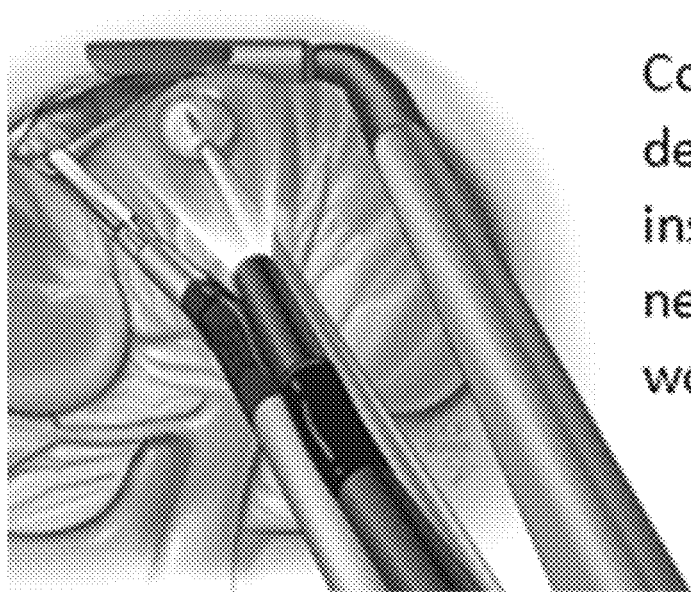
FIG. 2 shows conventional means to perform surgery via a single port (incision).

For example, Natural Orifice Translumenal Endoscopic Surgery (NOTES) and single-port laparoscopic surgery have been developed. NOTES relies on endoscopic tools to insert into natural orifices of the body and be skillfully maneuvered to perform specified tasks such as an appendectomy or cholecystectomy. Due to the limitations in endoscope tool mobility and control the range of procedures NOTES can be performed for is very limited and requires high level of expertise. Single-port laparoscopic surgery is similarly severely limited in mobility because creating the necessary angles for tools to work is limited by the size of the port and the tools controllable flexibility. The use of a single port means the tools must bend in limited space to create the necessary working angles as illustrated in FIG. 2. This creates a relatively small working area and makes the tools complex and difficult to control. For these reasons NOTES and single port laparoscopic surgery are not as widely performed compared to traditional laparoscopic procedures.

Over the last twenty years robotic systems for performing laparoscopic procedures have been developed and refined including the Zeus Surgical System (Computer Motion) and the Da Vinci Surgical System (DVSS; Intuitive Surgical Inc, Mountain View, Sunnyvale, CA). These systems allow the operator to separately view and remotely control the laparoscopic instruments. Sophisticated and intuitive controls have been developed to reduce the learning curve and allow for improved user precision compared to traditional manual laparoscopic instruments. The drawbacks of these systems are there high cost (approximately $1 million) and that they are similar to traditional laparoscopy in that they still require numerous incisions and are limited in mobility by the incision placement.

Figure 3:
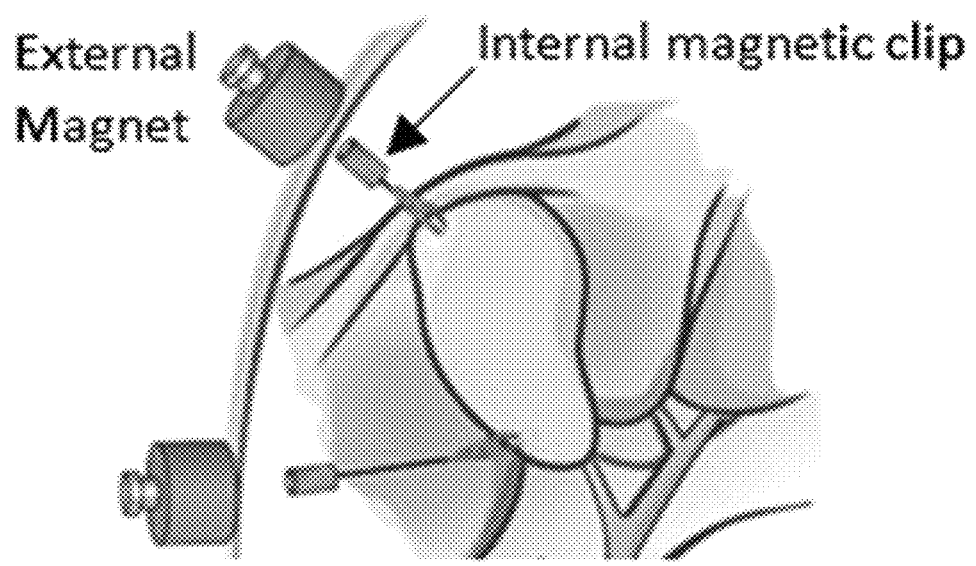
FIG. 3 shows conventional methods of using external magnets and internal magnetic clips to retract tissue away from the working area during laparoscopic surgery.

Utilization of external magnets and internal magnetic clips to retract tissue away from the working area during laparoscopic surgery, as shown in FIG. 3 can eliminate the need for one of the incisions during surgery and allow the clipped tissue to be freely positioned in the body. The concept of using magnetic clips has been FDA approved for use by Levita Magnetics (Menlo Park, CA). However, this procedure uses only passive clips and still requires multiple incisions and the use of limited mobility traditional laparoscopic tools that pass through multiple incisions.

In contrast, embodiments of the SIFM system can be configured to use magnetic force passing through the skin to eliminate all but one incision port while allowing for full range of user-controlled movement that is not limited to the port location as discussed in the following section. For instance, an embodiment of the single incision free motion (SIFM) laparoscopic surgical system, shown in FIG. 4, can provide significant surgical improvements and allow only a single incision to be utilized during surgery.

The embodiment of the SIFM system shown in FIG. 4 can split a traditional laparoscopic tool into two halves, half that goes outside the body and half that goes inside the body. The half inside the body can be placed through a single incision and then external magnetic plates can be positioned to sandwich the skin, holding it to the magnetic plate outside the skin. Constant and controllable force between the magnetic plates can be provided to control motion of the half within the human body during a procedure. This can help ensure the system is stable and the doctor can freely translate the device across the skin surface without being constrained to pivot around the incision port as in traditional laparoscopic surgery.

The grasping end effector of the embodiment of the SIFM system can be configured to universally tilt around the magnetic plate based on the movement of the handle. This tilting and depth can be sensed through position sensors: magnetic tracking sensors already available in PI Moore's Lab, Trakstar (NDI, Waterloo, Canada). With closed loop control the components inside the body can move in conjunction with the handle outside the body; thereby behaving as if this was one solid part passing through the skin. Low-profile electric motors and hydraulic actuation can be configured to allow for smooth and wide range of motion control of the components.

Embodiments of the SIFM system design can offer at least the following features to greatly benefit the procedure of laparoscopic surgery:
- Single small incision is made to allow for access of under skin instruments.
- Mobility is not limited to port location, tools and instruments are free to move as in open surgery. Therefore, required learning curve is reduced and achievable user precision is increased.
- This system can be used with robotic laparoscopic systems or it can be used by itself with the user manually controlling the outside body instruments.

As shown in FIG. 4, an embodiment of the SIFM system can hold together the inside and outside plates using magnetic force. The magnetic system can hold the plates together at a controlled pressure while still allowing for the plates to slide when the user wants to adjust the plate position on the skin surface.

In some embodiments, a real time magnetic clamping force control and a smooth sliding magnetic plate design can facilitate control of the tool(s) positioned within the human body for a surgical procedure.

Figure 5:
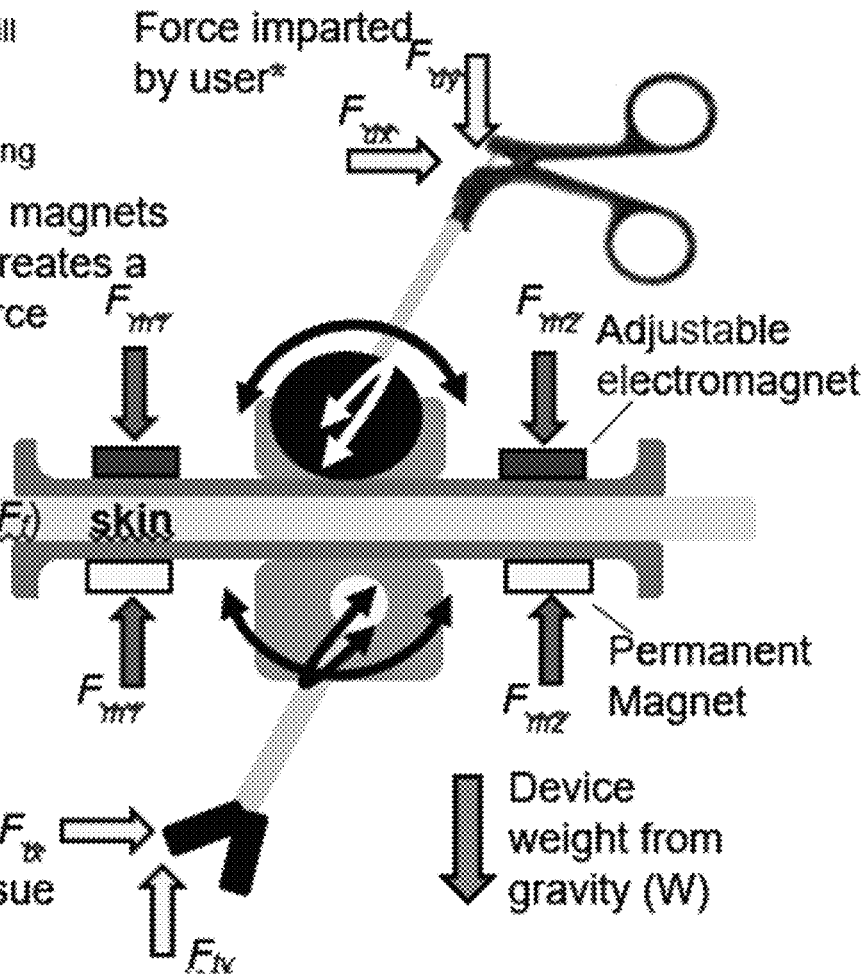
FIG. 5 shows a force model for an exemplary coupling arrangement between the first component and the second component of the tool.

A comprehensive force model can be developed to relate forces and device size parameters to how successfully the system can keep plates fixed and be able to slide across the skin during repositioning for use of the control system. For instance, as shown in FIG. 5, user forces ($F_{ux}$, $F_{uy}$, $F_{uz}$), frictional force ($F_f$), weight (W), and tissue forces ($F_{tx}$, $F_{ty}$, $F_{tz}$), and magnetic clamping forces ($F_{m1}$, $F_{m2}$, etc.) can all impact the system and the control of the system. These parameters can be used as inputs into the force model that can be used by the control system. Embodiments of this model can be put into a MATLAB (Natick, MA) function with a graphical user interface to allow for easy optimization and adjustment of all parameters; thereby allowing optimal device size, weight, electromagnetic force, and electric motor and hydraulic force to be chosen for control of the system during a surgical procedure.

The frictional force ($F_f$) is related to the coefficient of friction ($\mu$), and the total clamping force ($F_{MT}$) by: $F_f = F_{MT} * \mu$. Experimentation on porcine skin can be performed to define these parameters. A linear motor, Dunkermotoren (Bonndorf, Germany), can be configured to pull the porcine skin through two plates that pneumatically clamp down at varying pressures while a six-axis force sensor, ATI Industrial Automation (Apex, NC, Gamma IP65), measures both the $F_{MT}$ and $F_f$. Force sensor, pneumatic cylinders, and linear motor are available for use in PI Moore's laboratory so that the relationship between $F_f$ and $F_{MT}$ can be measured across numerous materials (Teflon, Stainless Steel, PEEK, etc.), different textures, different overall plate shapes, and different levels of lubrication. By changing the overall plate shape, such as making the plate slightly convex, the force distribution can be varied and therefore impact the sliding friction. This rigorous evaluation can provide strong justification for the material and design of the magnetic plates as well as provide data for use in the force model that may be utilized for control of the system for a particular embodiment of the system.

The size, number, and orientation of the electromagnets and permanent magnets for an embodiment of the SIFM system can be chosen along with the material type and texture for the plates.

Figure 6:
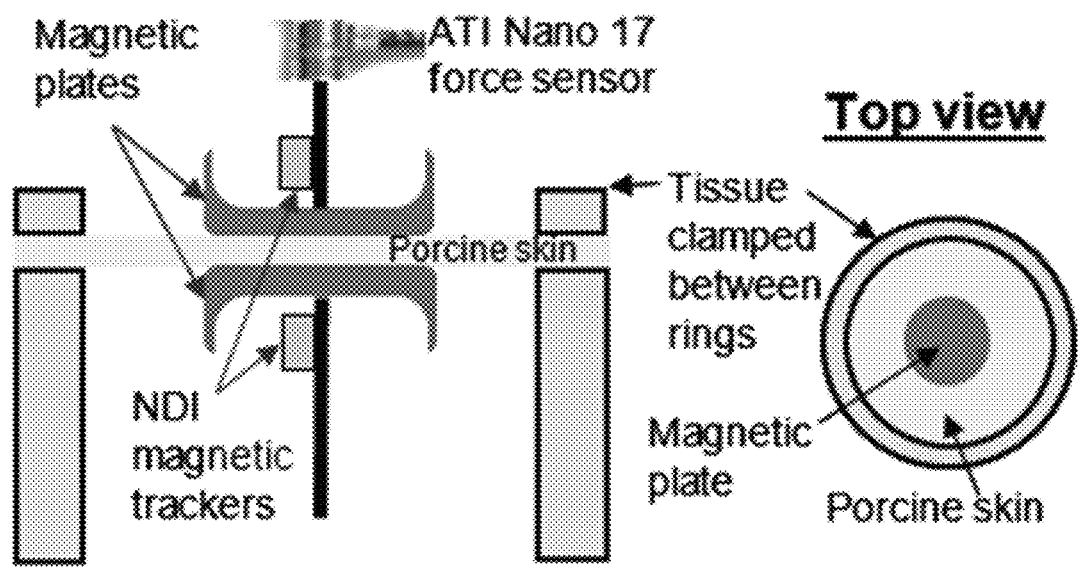
FIG. 6 shows an exemplary experimental set up to measure magnetic performance and tissue flexibility.

Porcine skin can be mounted in the air so that an embodiment of the SIFM system can be attached as shown in FIG. 6. Using miniature ATI Industrial Automation (Apex, NC, Nano 17) force sensor external force can be applied and stability and frictional force evaluated. Performance using both constant and variable magnetic forces can also be assessed. Alternating the amount of force at different electromagnets may reduce sliding friction while still allowing for securely holding the device in position. Such data that can be collected can be utilized in optimization of an embodiment of the SIFM system.

Embodiments of the SIFM system can be configured so that the controlled tiling and extending motion is low profile to allow for the end effector to reach near the skin surface; thereby maximizing the tools working area. Multiple separate systems of controlled motion can be utilized such as, for example: (1) use of hydraulic actuation for the extension and actuation of the end effector, and (2) use of low-profile high torque servo motors for the tilting of the device. Hydraulic actuation offers responsive compact linear motion, while servo motors offer compact accurate responsive controlled rotation, making them ideal for the proposed application.

In traditional laparoscopic surgery the range of motion (ROM) is a cone shape, where the tip of the cone is at the entry point. Uniquely SIFM offers free range of motion over the surface of the tissue and therefore the range of motion is a complete rectangle space with a minimum and maximum depth dictated by the device's extended and retracted distance.

In embodiments of the SIFM system, a geometric model can be defined to estimate space during insufflation. The model can define the range of motion (ROM) that may be necessary to perform a pre-specified laparoscopic procedure on varying patients of different sized (e.g. patients having different BMIs).

The flexibility of the porcine skin per surface area can also be estimated using the same setup discussed above to be used in conjunction with control of the SFIM system. Embodiments of the SIFM system can uniquely move beyond a motorized tilting range of motion because the tissue surface can be flexible between the magnetic plates as they tilt and move in and out. Tissue flexibility can be evaluated by applying force and moments to the magnetic clamped plates under varying constrained tissue surface areas and using available magnetic tracker sensors to measure the tissue movement and define control parameters for the SIFM system that takes into account skin flexibility.

As illustrated in FIG. 4, multiple magnetic trackers can allow for continual monitoring of the angle and position of the user handle relative to the controlled actuation. Feedback motor control can continuously minimize the difference in angle between these sensors, thereby allowing for responsive user control. An existing disposable laparoscopic tool and a low profile servo motor case designed to fit the servo motor gear train, high-power miniature DC motor, and potentiometer can be utilized in the SFIM system. Custom low profile hydraulic cylinders can also be utilized. The force modeling discussed above can be utilized to size the components and determine the gear ratio and hydraulic cylinder diameter for a particular SIFM embodiment to optimize it for a particular set of design criteria as well.

The magnetic trackers can also be used to accurately measure the position of the user inputs and controlled outputs to determine latency and maximum speed settings for the control system. In addition, forces can be measured to determine the stall force of the controlled actuation.

Embodiments of the SIFM system can have a large impact on laparoscopic surgery by allowing for freedom motion, reduced number of incisions, and user-friendly controls.

Example 2

Laparoscopic surgery is a common minimally invasive surgery that uses specialized tools to access the abdominal cavity and pelvic regions via small incisions called ports. Compared to open surgery, laparoscopy's small incision size better protects a patient's health and reduces recovery time. However, restricted rotation of the tools around chosen port locations can limit a surgeon's mobility while operating. In some cases, surgeons must lengthen or add ports which negates the positive health impacts. As a solution, the Novel Single Incision, Free Motion (SIFM) Laparoscopic Surgical System can increase the surgeon's range of motion and decrease the number of ports needed while keeping small incision sizes. This tool uses a strong and variable magnetic connection by using two permanent magnets on either side of the abdominal wall. A handheld external magnet can vary in height to control the strength of the connection between the external and internal tool components. The resulting planar joint enables the internal tool to translate and rotate against the inside of the abdominal wall. A cable system and stepper motors provide additional control of the tool's end effector. Testing evaluated the magnetic strength and resulting forces of the tool's magnetic system and analyzed the precision of the cable system. The SIFM system combines the health benefits of minimally invasive laparoscopic surgery with the free motion and ease of open surgery.

With the novel SIFM laparoscopic tool design, surgeons control the tools through the skin in an active fashion. FIG. 7 illustrates the tool's magnetic connection through an abdominal wall. The external tool is controlled by the operating surgeon and can move freely around the outside of the abdominal wall with an adjustable force between components. The internal tool can slide into the abdominal cavity via a port near the umbilicus. A cable system is fed through the port and controls the internal tool's end effector. A Teflon casing around both tools reduces the coefficient of friction when sliding across the skin. The SIFM laparoscopic system reduces the number of ports needed to a single incision, and enables free motion inside the abdominal wall.

Three different experiments generated data on the SIFM laparoscopic tool. Experiment 1 focused on optimizing the magnetic attractive force between the external and internal tools using Ansys (Canonsburg, Pennsylvania) simulation software. Experiment 2 analyzed the maximum applied forces and torques of the internal tool via the magnetic connection. Experiment 3 measured the precision of the cable system used to control the internal tool's end effector.

In Experiment 1, six magnetic permutations were calculated and compared against each other. The purpose of this experiment was to determine the optimal magnetic configuration that resulted in the strongest attraction force. Ansys simulations compared single pole magnets and dual pole magnets across three subcategories: axial, radial, and permeable disk. Because the single and dual pole magnets are outside of the body, they did not share the same limitations as the internal magnets. The simulations modeled the single pole magnets as two axially magnetized neodymium magnets with one north pole upward and the other south pole upward. The dual pole magnets were the same size as the single pole but were modeled as a magnet disk inside a magnetic ring, with the ring north pole upward, and center disk with south pole upward. The internal magnets were concentric with the external magnets and resided at a set distance away. To have easily comparable data, the sizes of each magnet and spacing apart remained the same in each permutation. The axial magnets are grade N-52 (residual induction of ~14.5 mT), the radial magnets are grade N-50 (residual induction of ~14.2 mT), and permeable disk is modeled as Cobalt-Iron (relative permeability of 18000). The axial magnets are from K&J Magnetics (Jamison, Pennsylvania), and radial magnets from SuperMagnetMan (Pelham, AL).

Both Experiments 2 and 3 utilized the SIFM device designed and fabricated as shown in FIG. 8. The SIFM device regulates the magnetic force with adjustable separation of the internal and external magnets. A user can adjust the external tool's height to account for muscle, fat, and tissue thickness changes while moving around the abdominal wall. The external system relies of feedback from two force sensing resistors (Pololu, Las Vegas, NV) that measure the attractive force between the internal and external magnets and can be adjusted on ranges from 0 mm to 38.1 mm. A set of two oppositely poled axial magnets are used in both tools. The magnets selected were grade N-52 neodymium magnets from K&J Magnetics. Rigid PLA plastic encased each set of magnets, and the base is wrapped in Teflon to reduce friction when sliding across skin and tissue. Extensive testing that evaluated low friction materials sliding over porcine skin determined Teflon as the desired material as reported in the DMD 2022 conference paper titled "Selection of Low Friction Material for Novel Single Incision, Free Motion Laparoscopic Surgical System." Additional control of the tools end effector is provided through a motor driven cable system. A spring joint attached the cable system and the tool to the magnetic base. Four-lumen lock line tubes created the tubing system that housed these cables.

Figure 9:
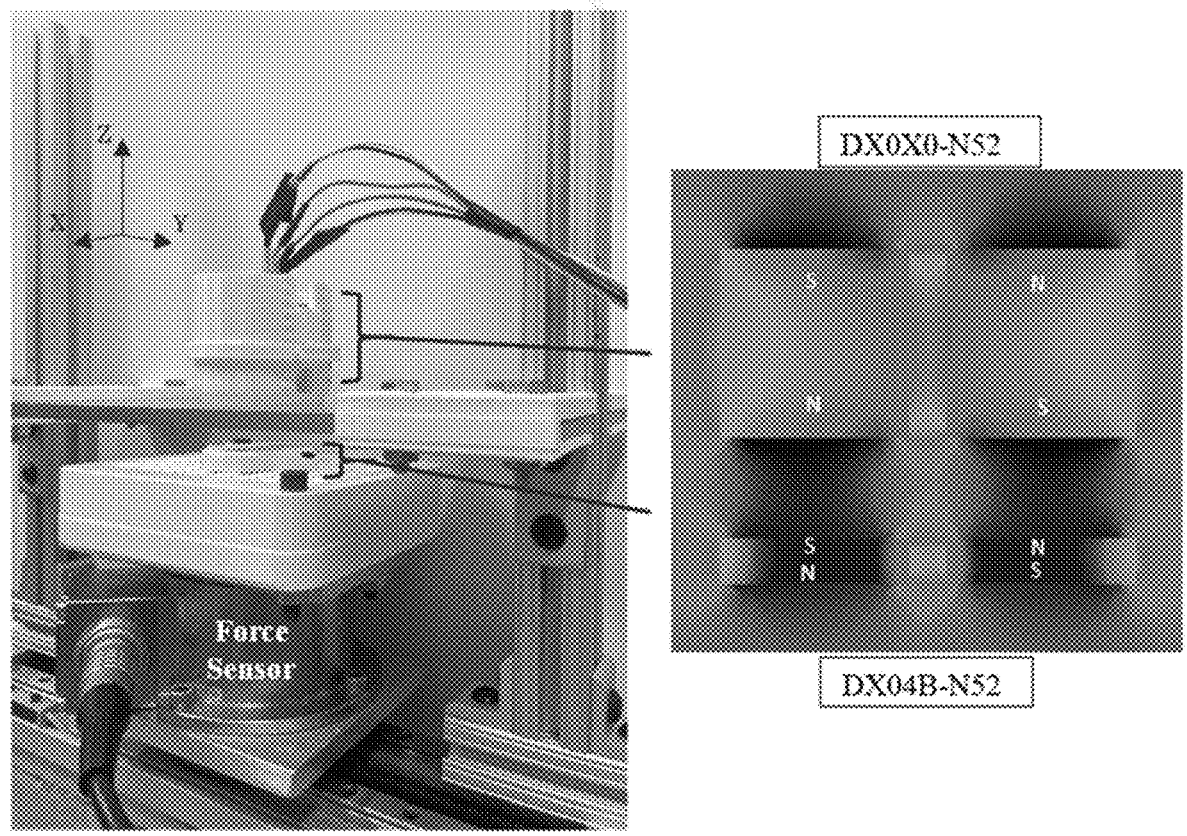
FIG. 9 shows an exemplary experimental setup to measure magnetic forces and torques in the x, y, and z directions.

Experiment 2 measured the maximum forces and torques of the magnetic system at different distances apart utilizing the SIFM device along with the experimental setup shown in FIG. 9. Magnetic position was varied in the x and y plane, and rotation about the z axis, while force was collected using the ATI Gamma IP65 force sensor (ATI Industrial Automation, Apex, North Carolina). Data collected in Experiment 2 was compared to calculated data from Ansys simulations. Both Ansys and sensor testing measured the forces and torques provided by the magnetic connection at separation distances from 9.525 mm-38.1 mm, with 3.175-mm increments.

The maximum force in the z direction occurs when the internal and external magnets are concentric, shown in the image on the right in FIG. 9. The maximum force in the x and y directions is found when the external tool is shifted along its respective axis. However, the shift along an axis reduces the force in the z direction. Therefore, at the maximum x and y forces, the maximum z force is recorded as well. The maximum torque was found by rotating the external tool around the z axis, again this rotation decreases the maximum z force. Testing recorded six forces and one torque at each separation distance. Experimental force results were compared to Ansys simulation results.

Figure 10:
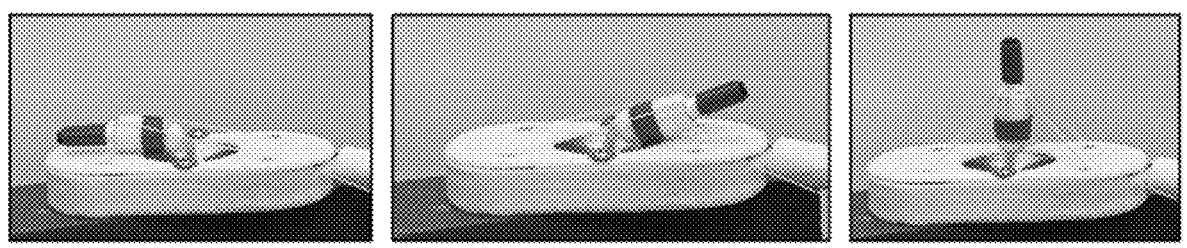
FIG. 10 displays three individual frames of video MATLAB used to analyze tool angle.

Experiment 3 measured the precision of the internal tool's end effector, controlled by a cable system and stepper motors. MATLAB (MathWorks, Natick, MA) analyzed the angle of the tool's end effector as it rotated about the x and y axis. The rotation about the x and y axis occurred independently of one another to keep the calculations simple. A video recorded tool's end effector rotating from approximately 180 degrees (horizontal) to 0 degrees, then back up to 90 degrees (vertical). FIG. 10 displays the three individual frames of the video MATLAB used to analyze the tool angle. The tool's tip and base are marked in red and blue. The centroid locations of the colored stripes are found in MATLAB and used to calculate the tool's angle. Data was collected on rotation about the y axis (images shown in FIG. 10.) and x axis.

Figure 11:
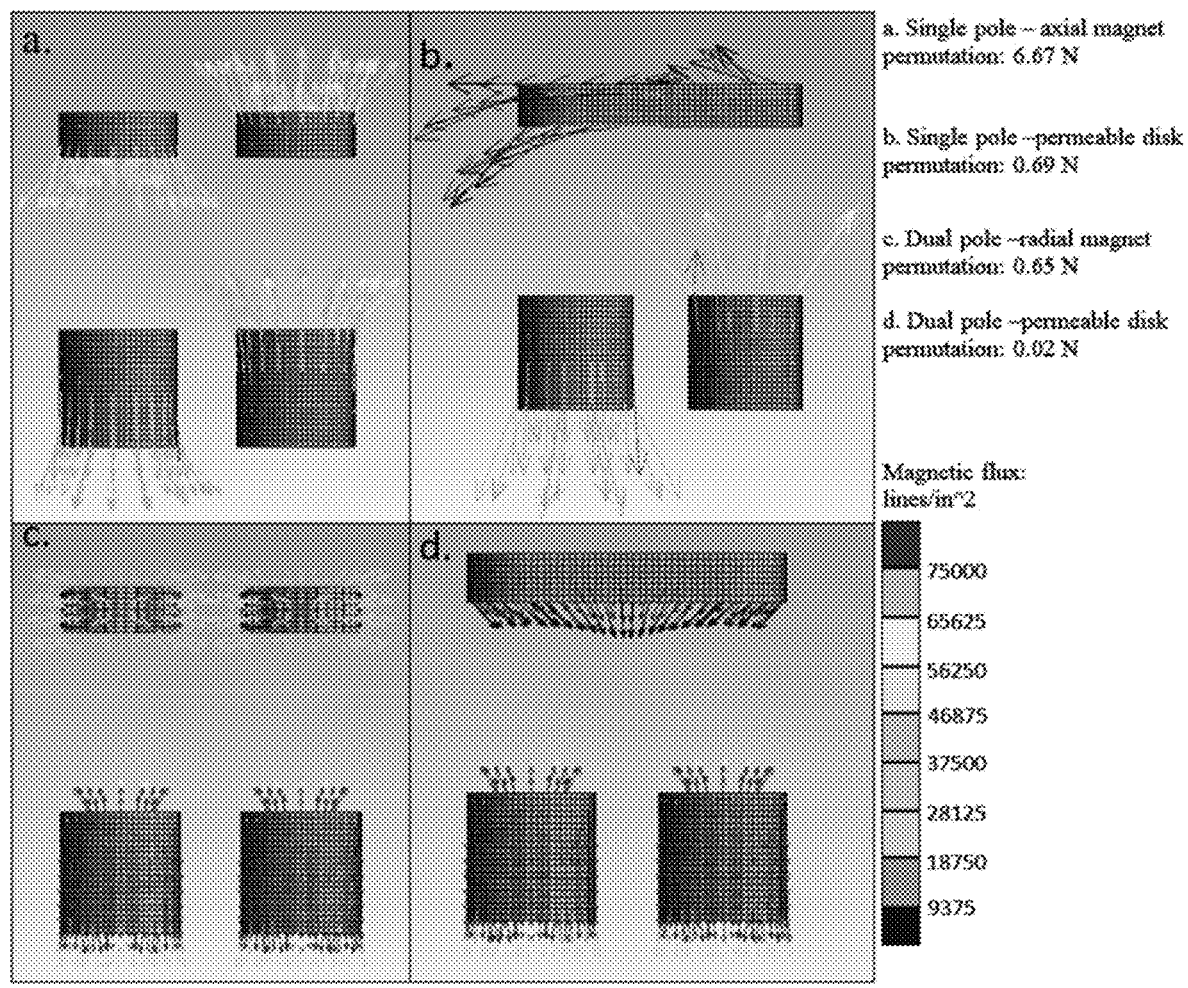
FIG. 11 displays the magnetic flux densities and resulting forces from Experiment 1.

The results from Experiment 1 created the design of the internal and external tools that Experiments 2 and 3 analyzed. Experiment 1 optimized the magnetic configuration of the internal and external tools with the use of Ansys's computer modeling software. FIG. 11 displays the magnetic flux densities and resulting forces from Experiment 1. The figure only contains four out of the six considered permutations and excluded the single pole external magnet-radial internal magnet, and dual pole-axial internal magnet configurations because their net force approached 0 N. In both excluded permutations, the magnetic configurations created counteractive magnetic fields which resulted in a net attractive force of around 0 N.

Figure 12:
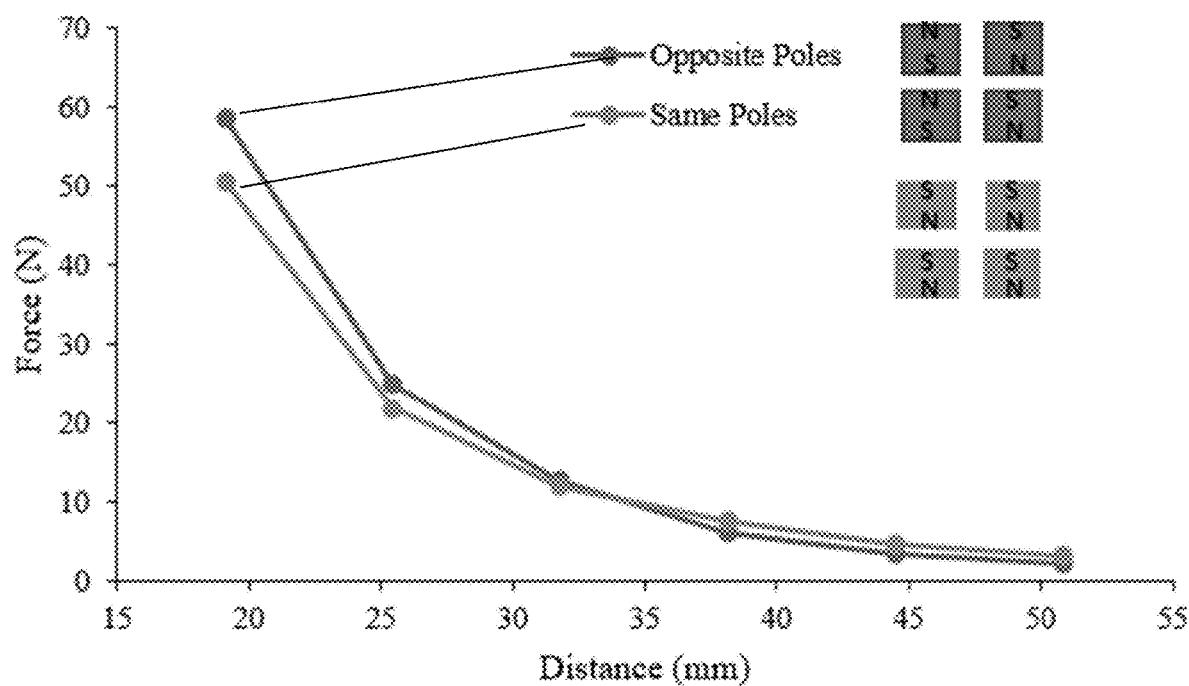
FIG. 12 shows a force comparison between two tests where the magnets were similarly poled, and another set oppositely poled.

The single pole configuration, shown in image (a) and image (b) of FIG. 11, provided higher forces at a separation distance of 38.1 mm than the dual pole configuration. For the magnet sizes chosen in this experiment, the single pole magnets were stronger at farther distances, and dual pole magnets were stronger at closer distances. Because muscle, fat, and tissue separates the internal and external tools during surgery, the SIFM design requires a magnetic configuration that is stronger at farther distances. The configuration with the highest force was the single pole-axial magnet configuration which produced 6.67 N. The single pole-permeable disk produced the second most force of 0.69 N. In future designs, a combination of permeable disk and axial internal magnet will produce additional magnetic forces. Furthermore, a magnetic yoke could become a potential alternative instead of an external permanent single pole axial magnet. With a magnetic yoke, the field easily adjusts with a change in current, instead of the current system that relies on adjusting the magnets height to control forces between the internal and external magnets. One method to increase holding force of the single pole-axial configuration would be to make both sets of magnets similarly poled, both the magnet's north pole would face downward. FIG. 12 provides a force comparison between two tests where the magnets were similarly poled, and another set oppositely poled. Although the opposite poled design creates weaker forces at farther distances, it provides a far stronger torque compared to the similar poled magnets. When both poles are the same, there is no repelling force when the external magnet rotates, resulting in very weak torques on the internal magnet. The chosen internal magnets minimized the magnets sizing while obtaining the necessary forces needed for surgery.

Figure 13:
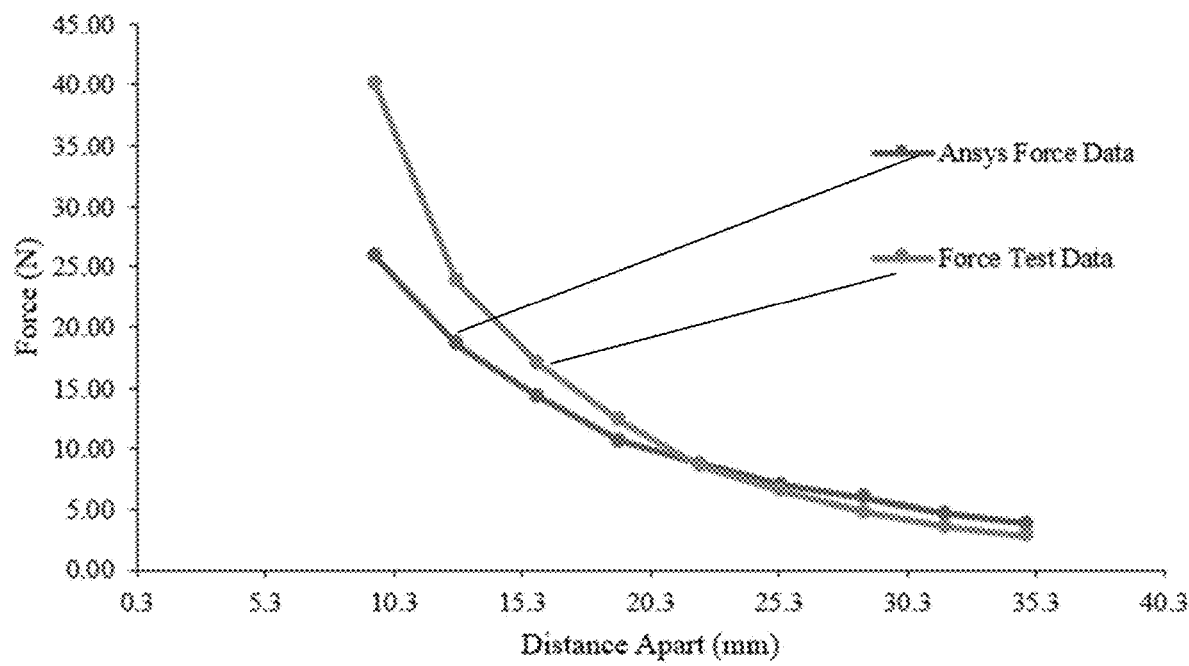
FIG. 13 illustrates the values for the maximum pulling force for both Ansys simulation and experimental data.

Experiment 2 tested the 3 forces and torques for the single pole-axial magnetic configuration and was compared to calculated results from the Ansys simulations. Table 1 presents the data for Experiment 2 and FIG. 13 illustrates the values for the maximum pulling force for both Ansys simulation and experimental data. There is minimal error in the calculated data vs experimental data after around 19.05 mm. However, the error in the first four data sets can be accounted for by the chosen meshing size of the calculated data and the chosen residual flux density. For a grade N-52 neodymium magnet, the typical residual flux density is between 1430-1480 mT. More additional error arose when purchasing magnets because there is no standard practice for measuring the grade of a magnet. In this case, we can assume the residual flux density resides on the upper range because the experimental data collected was higher than the calculated data. A more refined mesh would decrease the error in the data set as well but increases simulation time considerably.

TABLE 1

Forces and torques of the magnetic system from 9.5 mm to 38.1 mm

| Separation Distances (mm) | Max Force in X (N) | Max Force in Y (N) | Max Force in Z (N) | Z force at max X orientation (N) | Z force at max Y orientation (N) | Torque about Z axis (N-m) | Z force at max torque (N) | Ansys max Z force (N) |
|---|---|---|---|---|---|---|---|---|
| 9.5 | 22.25 | 15.50 | 40.00 | 21.00 | 33.00 | 0.38 | 38.75 | 25.81 |
| 12.7 | 16.25 | 6.75 | 23.75 | 11.25 | 21.00 | 0.31 | 17.35 | 18.63 |
| 15.9 | 12.25 | 5.00 | 17.00 | 7.75 | 15.50 | 0.25 | 12.00 | 14.27 |
| 19.1 | 8.00 | 3.50 | 12.35 | 5.15 | 9.40 | 0.20 | 5.85 | 10.58 |
| 22.2 | 6.00 | 2.50 | 8.50 | 3.60 | 7.00 | 0.14 | 5.30 | 8.70 |
| 25.4 | 4.20 | 2.10 | 6.42 | 2.60 | 4.30 | 0.09 | 4.00 | 6.92 |
| 28.6 | 3.25 | 1.75 | 4.75 | 2.20 | 3.50 | 0.07 | 3.35 | 5.92 |
| 31.8 | 2.30 | 1.50 | 3.50 | 1.60 | 3.10 | 0.05 | 2.20 | 4.62 |
| 34.9 | 1.85 | 1.30 | 2.80 | 1.20 | 2.35 | 0.04 | 2.00 | 3.78 |
| 38.1 | 1.50 | 0.60 | 2.30 | 0.80 | 2.00 | 0.03 | 1.80 | |

Figure 14:
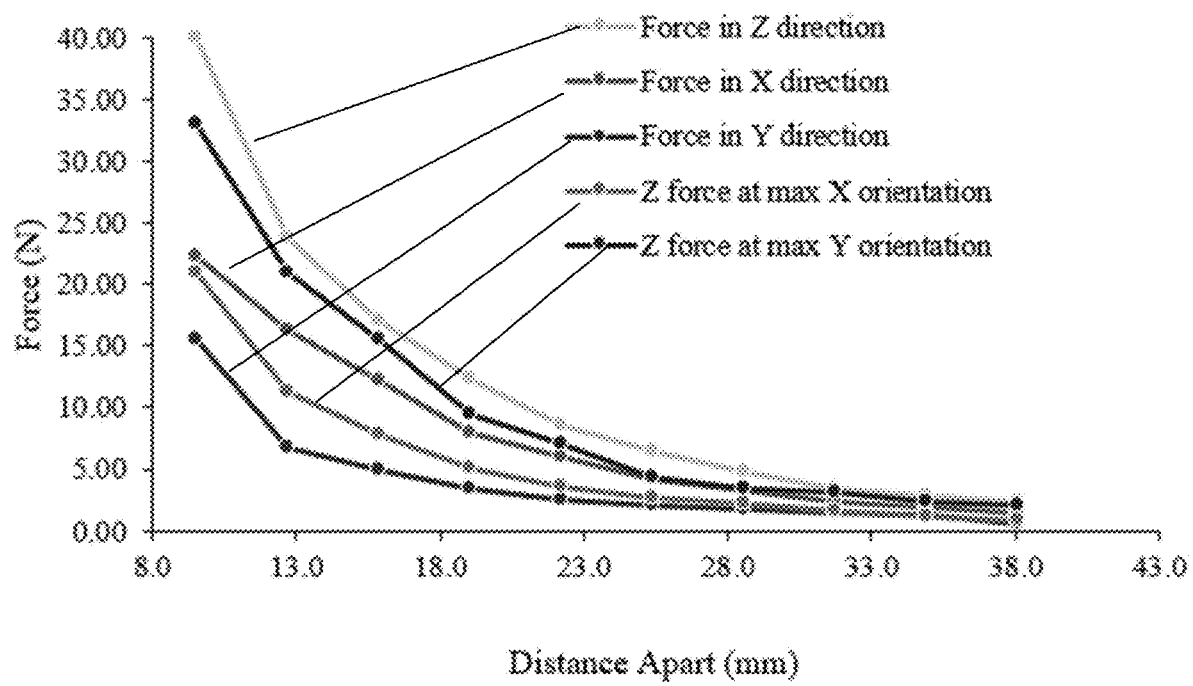
FIG. 14 shows experimentation results for maximum forces in the x, y, and z directions of the internal tool.

The force decreases exponentially as the distance between internal and external magnets increases from 9.525 mm to 38.1 mm, resulting in forces of 40 N down to 2.22 N respectively. The maximum forces in the x and y directions as well as torque decreases at an exponential rate similar to decrease in force in the z direction. FIG. 14 visualizes the relationships between maximum forces at each separated distance. Testing noticed that the applied force in the x direction is around twice the force applied in the y direction for all distances. However, the attractive force when the maximum force is applied in the x direction, is about half the attractive force when the maximum force is applied in the y direction. The magnetic configuration caused this difference in x and y directional forces. A shift in the x axis causes an additional repelling force from the internal magnet with north pole facing upward, and the external magnet with north facing downward. As the north pole of the external magnet started to shift over the north pole of internal magnet, there is more force provided in the x direction and less holding force because of the resultant repulsive force.

In practice, layers of muscle, fat, and skin tissue would separate the magnets. Depending on the location of the magnet in the abdomen, the rectus abdominus, or internal and external obliques, and the transverse abdominis would separate the internal and external tools. On average the rectus abdominus and transverse abdominis muscle is approximately 14.9 mm thick in men, and 12.2 mm thick in women. The average transverse abdominis and external and internal oblique thickness is approximately 19.1 mm in men and 14.4 mm in women. There is limited data on fat thickness because it varies drastically based on the patient and is highly compressible. However, skin and subcutaneous tissue thickness can range from 2.20-28.05 mm in males and 5.15-27.40 mm in females. For full range of motion in the abdominal wall, the laparoscopic tool would function effectively on patients with a skin and subcutaneous tissue thickness of less than approximately 6.35 mm in males and 11 mm in females. About 4 N of force is needed to cut into porcine ascending aorta tissue which is similar to human tissue aged under 60. As shown in FIG. 13, at a separation distance of 25.4 mm, the maximum force applied in the x direction is 6.4 N, a force greater than the required force to cut into porcine skin. When the force in the x direction is maximized at 25.4 mm, the holding force is 2.6 N. When no force is applied in the x or y direction, the maximum holding force increases to 6.4 N. Therefore, the expected holding force when cutting at the maximum separation distance assumedly resides between 2.6 N and 6.4 N. To summarize, the SIFM external tool can provide sufficient cutting force (up to 6.4 N in the x direction) on ascending aorta tissue, while maintaining between 2.6 N to 6.4 N of holding force.

Figure 15:
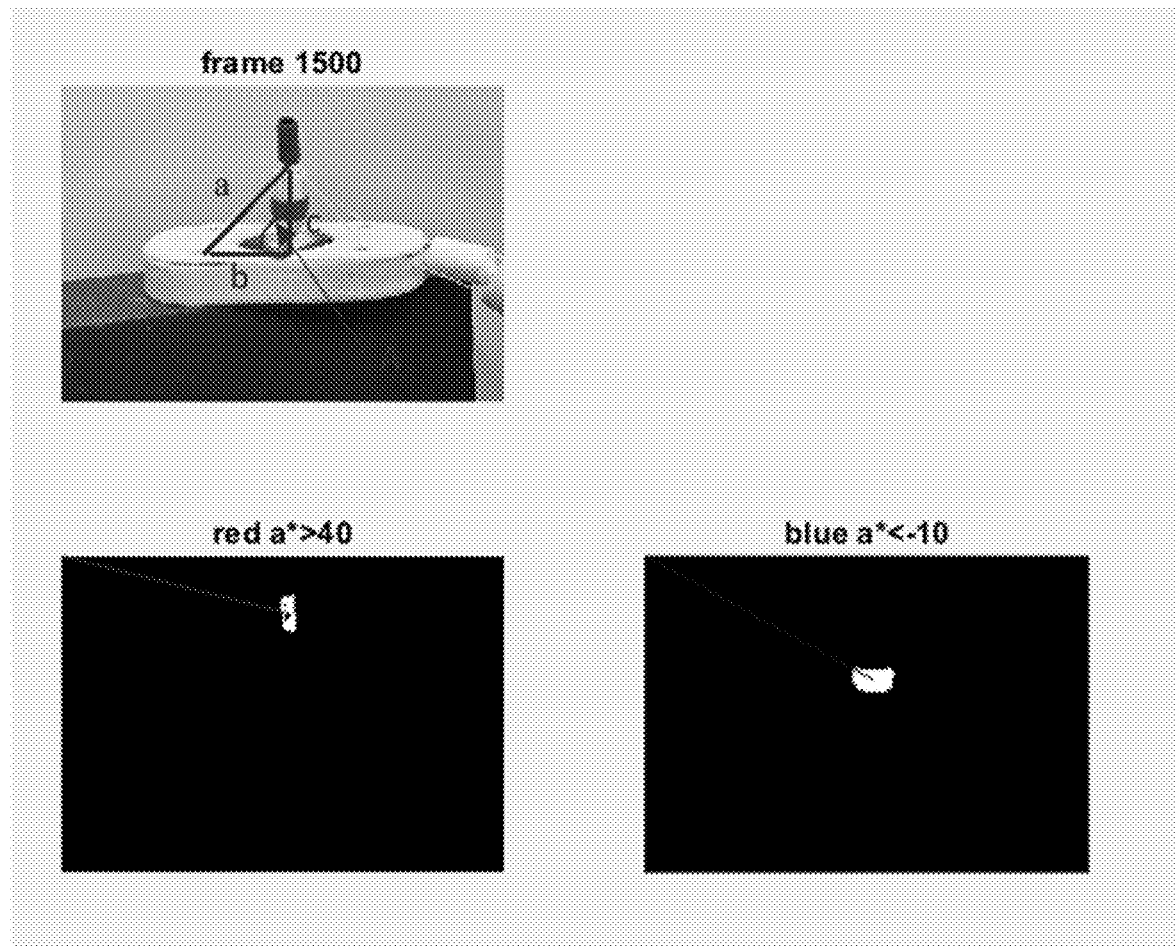
FIG. 15 presents a video frame of the tool rotation around the y axis.

Experiment 3 tested the precision of the stepper motor cable system. This experiment used four Nema 17 stepper motors (STEPPERONLINE, New York, NY), each with a maximum torque of 45 N-cm. A tubing system connected the internal tool and the four stepper motors. Several different types of tubes were tested before a rigid, four lumen tube was chosen. During tool control, the tube can bend freely. As the tube bends, one cable will become more slacked, and the cable on the other side of the tube will be taut. A four-lumen tube is crucial to keep the cables separated, otherwise the overlapping of the cables would prevent the tool from moving. Furthermore, a lock line system allows bending while keeping the material rigid. If the cables were housed by a rubber-like tubing system, there would be higher friction between the cables and rubber interior wall. The resulting high friction would stop the movement of the cables and thus the end effector. A more flexible tube allows for easier deflection of the internal system instead of pulling the cable through the tube and moving the end effector. With each cable attached to an individual stepper motor, the motor can account for slack or tension that occurs during operation of the tool. FIG. 15 presents a video frame of the tool rotation around the y axis. Testing compared the precision of the cable system during experimentation to the calculated tool precision. Each step from the stepper motor caused the cable to change in length. This change in cable length was used in the law of cosines equation, Eq. (1). to calculate the angle of the tool at each motor step. The law of cosines calculates the resulting angle between the base and the tool (A), $$A = (\cos^{-1}(b^2 + c^2 - a^2)) * \frac{1}{2*b*c} \quad (1)$$

where a, b, and c are sides of the triangle formed by the cable, base, and tool respectively. MATLAB used the position of the red and blue bands displayed in FIG. 15 to find the centroid of the colors and manually calculate the angle. The images titled "red a*>40" and "blue a*<−10" display what MATLAB sees. The left image highlights the red band, and the blue image highlights the blue band. FIG. 15 displays one video frame of the tool moving smoothly from 180 degrees (horizontal) to 0 degrees, then back to 90 degrees.

Figure 16:
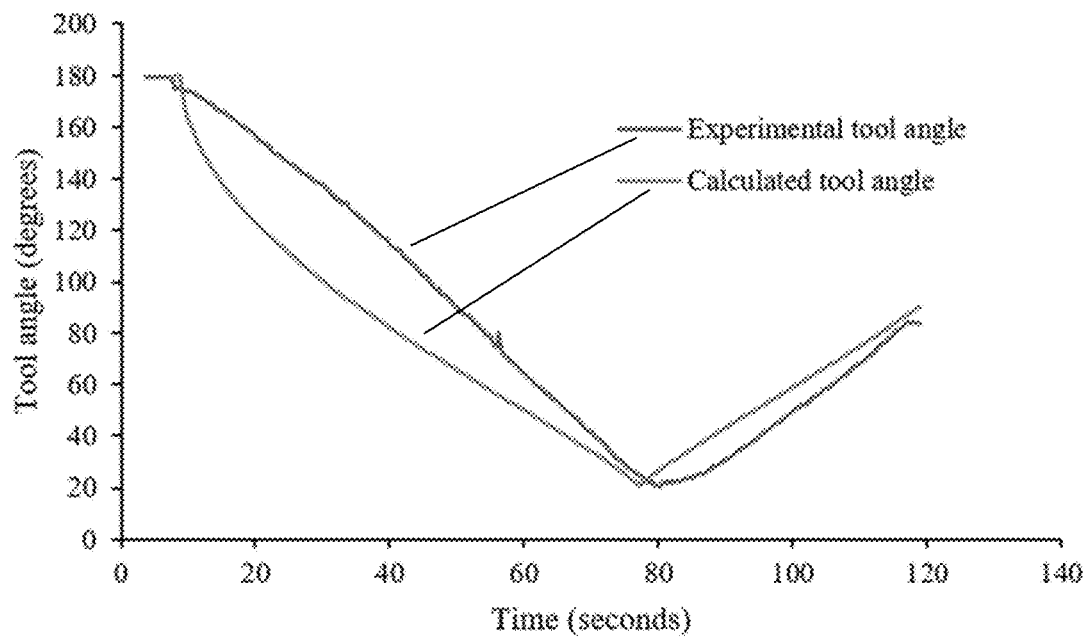
FIG. 16 illustrates the calculated tool angle and the experimental angle as the tool rotates around the y axis.

When inserted into the body, the tool will lay horizontal to reduce the overall profile. The insertion profile is 29 mm wide, and 10 mm tall, in addition to the area of the surgical tool attached to the end effector. At each frame of the video, MATLAB records the pixel locations of the bands to gather experimental position data on the tool angle. FIG. 16 illustrates the calculated tool angle and the experimental angle as the tool rotates around the y axis. The calculated plot shares a similar shape to the experimental plot but shifted to the right. This shift indicates a delay in the experimental tool's response time to the stepper motors changing the cable length.

Figure 17:
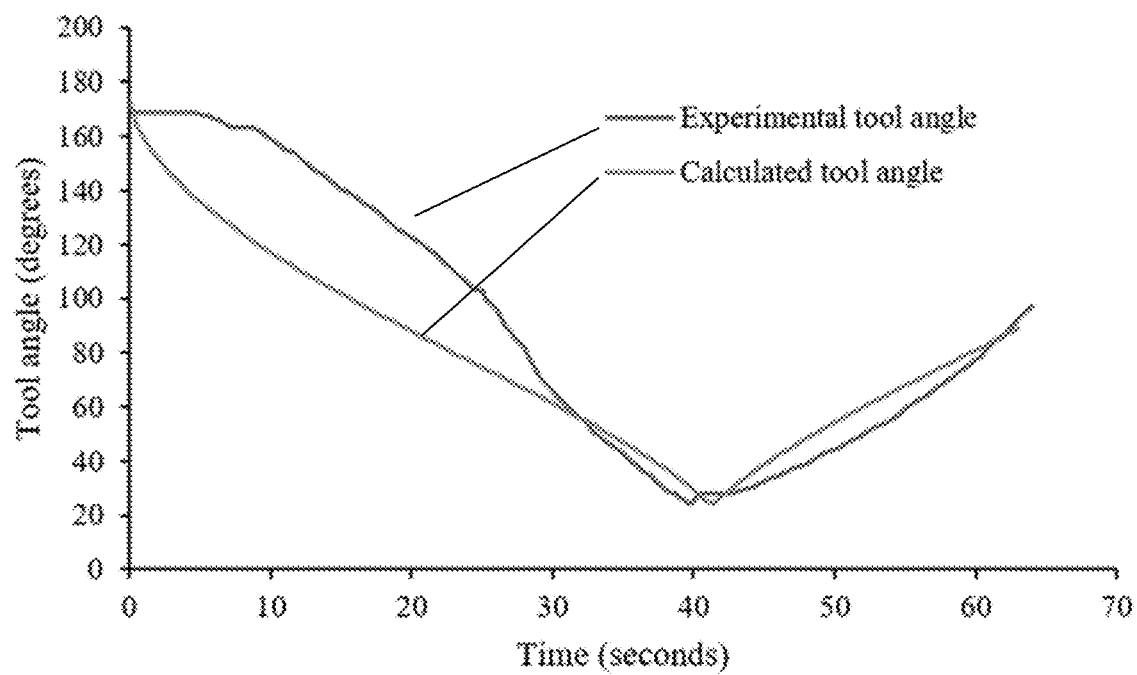
FIG. 17 illustrates the tool response for the rotation about the x axis.

After the 8 second mark and before the 70 second mark, the calculated plot predicts a quicker angle adjustment. This relationship is shown by the calculated data being several degrees lower than the experimental data and a steeper slope on the calculated tool angle. The stepper motors picking up slack in the cable caused the initial delay of the experimental data. The longer the cable and tube system, the more delay can be expected between direction changes of the tool. This delay does not present a problem in the system because the response time does not change the accuracy of the tool's position, but only changes the time for the tool to react. During rotation about the y axis, each step from the stepper motor is 1 degree at maximum, and when the tool adjusts for slack, each step will move the tool less than 1 degree. In practice, cameras and/or other sensors can inform the surgeon the tool's location. At 80 seconds on the plot, the tool reaches the end of its rotation and starts moving back upward to 90 degrees. After the 80 second plot, the delay in rotation occurs again as the experimental data takes more time to move compared to the calculated data. FIG. 17 illustrates the tool response for the rotation about the x axis. Because the cable port locations are placed closer to the base of the end effector, the rotation about the x axis is less precise than the rotation about the y axis.

Each step from the motor results in about two degrees of motion in the tool's angle. For rotation about the y axis, rotations require about 80 seconds, compared to the 40 seconds spent rotating about the x axis. The y rotation plot, as seen in FIG. 17, displays the same delay relationship as the rotation delay about the x axis. The results supported that a step will be less than a degree of rotation of the tool when rotating about the y axis. Similarly, a step in about the x axis will result in less than 2 degrees in rotation of the tool. During large movements, the law of cosines equations (1), can model the shape of the tool's rotation with the cable length as the dependent variable. If the tool rotate about multiple axis, the tool's height would become another dependent variable.

The Novel Single Incision, Free Motion (SIFM) Laparoscopic Tool used an optimized magnetic configuration to minimize the internal tool's profile while maintaining a strong magnetic connection through the skin. The second experiment analyzed the resulting forces and torques of the planar joint created by the magnetic connection to determine the maximum skin and subcutaneous tissue thickness where the SIFM tool could sustain strong enough attractive forces. The external tool provides feedback on the forces between the magnets and the height can be adjusted to optimize the magnetic connection. The internal tool can apply the necessary forces required in laparoscopic surgery when the overall distance between the internal and external tool is less than or equal to 25.4 mm. The third experiment analyzed the precision of the tool's end effector controlled by the cable system. With stepper motor control provided outside of the body, the end effector will rotate no more than 1 degree about the x axis and no more than 2 degrees about the y axis for each motor step.

Each of the following references is incorporated herein by reference in its entirety.

[1] Wood, Laura. "Global Laparoscopy and Endoscopy Devices Market, 2025-Focus on Surgical Procedures (Cholecystectomy and Hysterectomy) and Product Types (Arthroscopes, Neuroendoscopes, Cystoscope, and Bronchoscopes)," Research and Markets, 2018, https://www-.globenewswire.com/news-release/2018/09/19/1572863/0/en/Global-Laparoscopy-and-Endoscopy-Devices-Market-2025-Focus-on-Surgical-Procedures-Cholecystectomy-and-Hysterectomy-and-Product-Types-Arthroscopes-Neuroendoscopes-Cystoscope-and-Bro.html.

[2] Vecchio, MacFayden; Palazzo, R; B V; F. "History of Laparoscopic Surgery." *Panminerva Medica*, U.S. National Medicine, March 2000, Library of https://pubmed.ncbi.nlm.nih.gov/11019611/.

[3] F. S. Tsai et al., "Fluidic lens laparoscopic zoom camera for minimally invasive surgery," *J Biomed Opt*, vol. 15, no. 3, p. 030504, May-June 2010.

[4] McMillan, Alissa. "Minimally Invasive Surgery vs. Open Surgery: What's the Difference?" *Evansville Surgical Associates*, 14 Jan. 2021, https://www.evansville-surgical.com/minimally-invasive-surgery-vs-open-surgery-whats-the-difference/.

[5] R. Veldkamp et al., "Laparoscopic surgery versus open surgery for colon cancer: short-term outcomes of a randomised trial," *Lancet Oncol*, vol. 6, no. 7, pp. 477-84, July 2005.

[6] F. P. Secin et al., "The learning curve for laparoscopic radical prostatectomy: an international multicenter study," *J Urol*, vol. 184, no. 6, pp. 2291-6, December 2010.

[7] F. P. Secin et al., "The learning curve for laparoscopic radical prostatectomy: an international multicenter study," *J Urol*, vol. 184, no. 6, pp. 2291-6, December 2010.

[8] R. Berguer, W. Smith, and Y. Chung, "Performing laparoscopic surgery is significantly more stressful for the surgeon than open surgery," *J Surgical endoscopy*, vol. 15, no. 10, pp. 1204-1207, 2001

[9] "Levita Magnetics Announces FDA Clearance of Expanded Indication for Magnetic Surgical System for Use of Bariatric Procedures." *Levita Magnetics Announces FDA Clearance of Expanded Indication for Magnetic Surgical System for Use in Bariatric Procedures|Business Wire*, 22 Oct. 2018, https://www.businesswire.com/news/home/20181022005267/en/Levita%C2%AE-Magnetics-Announces-FDA-Clearance-of-Expanded-Indication-for-Magnetic-Surgical-System-for-Use-in-Bariatric-Procedures

[10] Wells, Ali, et al. "Laparoscopic Surgeons' Perspectives on Risk Factors for and Prophylaxis of Trocar Site Hernias: A Multispecialty National Survey." *JSLS: Journal of the Society of Laparoendoscopic Surgeons*, Society of Laparoendoscopic Surgeons, 2019, https://www.ncbi.nlm.nih.gov/pmc/articles/PMC6532834/.

[11] Xue, Renfeng, et al. "A Cable-Pulley System Modeling Based Position Compensation Control for a Laparoscope Surgical Robot." *Mechanism and Machine Theory*, Pergamon, 1 Sep. 2017, https://www.sciencedirect.com/science/article/pii/S0094114X1730900X?casa_token=0_OSdoPyJLMAAAAA%3ApfdbkdydnOY0ynRpyFRtjualMnkSiLGSuVrqODn5cNVaAnmkyJ1XxjInwiZndUO9ZxLmHzGu6Haq.

[12] Hu, Zhongwei, et al. "Characterization of Aortic Tissue Cutting Process: Experimental Investigation Using Porcine Ascending Aorta." *Journal of the Mechanical Behavior of Biomedical Materials*, U.S. National Library of Medicine, February 2013, https://www.ncbi.nlm.nih.gov/pmc/articles/PMC3557667/.

[13] Hector W. L. de Beaufort et al. "Comparative Analysis of Porcine and Human Thoracic Aortic Stiffness" *Eur J Vasc Endovasc Surg*, no. 55 pp. 560-566, 2018.

[14] Tahan, Nahid, et al. "Measurement of Superficial and Deep Abdominal Muscle Thickness: An Ultrasonography Study." *Journal of Physiological Anthropology*, BioMed Central, 23 Aug. 2016, https://www.ncbi.nlm.nih.gov/pmc/articles/PMC4995748/.

[15] Störchle, Paul, et al. "Measurement of Mean Subcutaneous Fat Thickness: Eight Standardised Ultrasound Sites Compared to 216 Randomly Selected Sites." *Scientific Reports*, Nature Publishing Group UK, 2 Nov. 2018, https://www.ncbi.nlm.nih.gov/pmc/articles/PMC6214952/.

[16] Jain, Sunil M, et al. "Evaluation of Skin and Subcutaneous Tissue Thickness at Insulin Injection Sites in Indian, Insulin Naïve, Type-2 Diabetic Adult Population." *Indian Journal of Endocrinology and Metabolism*, Medknow Publications & Media Pvt Ltd, September 2013, https://www.ncbi.nlm.nih.gov/pmc/articles/PMC3784870/#:~:text=The%20range%20of%20skin%20%2B%20subcutaneous,in%20females%20%5BTable%2010%5D.

[17] Yamanaka, Hiroyuki, et al. "Measurement of the Physical Properties during Laparoscopic Surgery Performed on Pigs by Using Forceps with Pressure Sensors." *Advances in Urology*, Hindawi Publishing Corporation, 2015, https://www.ncbi.nlm.nih.gov/pmc/articles/PMC4346692/.

It should be understood that the disclosure of a range of values is a disclosure of every numerical value within that range, including the end points. It should also be appreciated that some components, features, and/or configurations may be described in connection with only one particular embodiment, but these same components, features, and/or configurations can be applied or used with many other embodiments and should be considered applicable to the other embodiments, unless stated otherwise or unless such a component, feature, and/or configuration is technically impossible to use with the other embodiment. Thus, the components, features, and/or configurations of the various embodiments can be combined together in any manner and such combinations are expressly contemplated and disclosed by this statement.

It will be apparent to those skilled in the art that numerous modifications and variations of the described examples and embodiments are possible considering the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof.

It should be understood that modifications to the embodiments disclosed herein can be made to meet a particular set of design criteria. Therefore, while certain exemplary embodiments of the apparatus and methods of using and making the same disclosed herein have been discussed and illustrated, it is to be distinctly understood that the invention is not limited thereto but may be otherwise variously embodied and practiced within the scope of the following claims.

What is claimed is:

1. A laparoscopic apparatus, comprising:
   a tool comprising a first component and a second component, wherein:
      the first component comprises: a first component manipulation end configured for manipulation by a user and/or a machine; and a first component interface end, wherein the first component includes:
         a first component magnet located at or near the first component interface end;
         a first component actuator system including a cable, the first component actuator system configured to transfer control movements from the first component manipulation end into moments and forces acting upon the cable;
      the second component comprises: a second component working end configured for performing surgical work; and a second component interface end, wherein the second component includes:
         a second component magnet located at or near the second component interface end;
         a second component actuator system configured to transfer moments and forces acting upon the cable into mechanical movements acting upon the second component working end.

2. The laparoscopic apparatus of claim 1, wherein:
   the first component is configured for use within an environment outside a human or animal body; and
   the second component is configured for use within an environment inside a human or animal body.

3. The laparoscopic apparatus of claim 2, wherein:
   the second component is configured to be enveloped or engulfed within a cavity of the human or animal body.

4. The laparoscopic apparatus of claim 2, wherein:
   when the first component interface end is placed on or near an outside skin surface of the human or animal body and the second component interface end is placed on or near an inside skin surface of the human or animal body such that the first component magnet and the second component magnet are in proximity to each other so as to allow the first component magnet to impose an attractive force on the second component magnet, the second component becomes coupled with the first component.

5. The laparoscopic apparatus of claim 4, wherein:
   when the second component becomes coupled with the first component, lateral movement, longitudinal movement, rotational movement, and/or tilt movement of the first component is translated to corresponding lateral movement, longitudinal movement, rotational movement, and/or tilt movement for the second component.

6. The laparoscopic apparatus of claim 1, wherein:
   the first component manipulation end includes a handle-actuator configured for use by a human hand and/or an adaptor configured to connect to a mechanical actuator of the machine.

7. The laparoscopic apparatus of claim 1, wherein:
   the second component working end includes an end effector.

8. The laparoscopic apparatus of claim 1, wherein:
   the first component magnet comprises one or more magnets;
   the second component magnet comprises one or more magnets; and
   the first component actuator system comprises one or more cables, one or more hydraulic actuators, and/or one or more electric motor actuators.

9. The laparoscopic apparatus of claim 1, wherein the first component interface end and/or the second component interface end includes one or more sensors.

10. The laparoscopic apparatus of claim 9, wherein the one or more sensors include a pressure sensor, a proximity sensor, a movement sensor, magnetometer, magnetic tracker, gyroscope, and/or an accelerometer.

11. The laparoscopic apparatus of claim 1, further comprising:
   a first component processor configured to control magnetic force of the first component magnet and/or a second component processor configured to control magnetic force of the second component magnet, wherein:
      magnetic force of the first component magnet is controlled via varying a distance the first component magnet is relative to the second component magnet and/or controlling current supplied to the first component magnet; and/or
      magnetic force of the second component magnet is controlled via varying a distance the second component magnet is relative to the first component magnet and/or controlling current supplied to the second component magnet; and
   a control module in communication with the first component processor and/or the second component processor, the control module configured to transmit a control signal to the first component processor and/or the second component processor.

12. The laparoscopic apparatus of claim 1, wherein:
   the first component interface end includes a layer comprising polytetrafluoroethylene.

13. A laparoscopic apparatus, comprising:
a laparoscope, the laparoscope comprising an actuator system including an actuator and a cable, the actuator system configured to transfer control movements from the actuator into moments and forces acting upon the cable;
a tool comprising a first component and a second component, wherein:
the first component comprises a first component interface end and a first component magnet located at or near the first component interface end;
the second component comprises: a second component working end configured for performing surgical work; and a second component interface end, wherein the second component includes:
a second component magnet located at or near the second component interface end;
a second component actuator system configured to transfer moments and forces acting upon the cable into mechanical movements acting upon the second component working end.

14. The laparoscopic apparatus of claim 13, wherein:
the first component is configured for use within an environment outside a human or animal body; and
the second component is configured for use within an environment inside a human or animal body.

15. The laparoscopic apparatus of claim 13, wherein:
the second component is configured to be enveloped or engulfed within a cavity of the human or animal body.

16. The laparoscopic apparatus of claim 13, wherein:
when the first component interface end is placed on or near an outside skin surface of the human or animal body and the second component interface end is placed on or near an inside skin surface of the human or animal body such that the first component magnet and the second component magnet are in proximity to each other so as to allow the first component magnet to impose an attractive force on the second component magnet, the second component becomes coupled with the first component.

17. A method of preparing for or performing a surgical procedure using a tool comprising a first component and a second component, the method comprising:
inserting the second component into a cavity of a body via an incision, wherein a cable extends from a second component actuator system through the incision and to a first component actuator system;
placing a first component interface end of the first component adjacent an outside skin surface of the body; and
allowing a magnet of the first component interface and a magnet of the second component interface to couple the first component with the second component.

18. The method of claim 17, further comprising:
performing surgical work within the body cavity by controlling a working end of the second component via actuation of a manipulation end of the first component.

19. The method of claim 18, wherein:
actuation of the manipulation end of the first component involves manual actuation via a human and/or automated actuation via a machine.

20. The method of claim 18, further comprising:
controlling lateral movement, longitudinal movement, rotational movement, and/or tilt movement of the second component via a corresponding lateral movement, longitudinal movement, rotational movement, and/or tilt movement of the first component.

* * * * *